(12) United States Patent
Dowdy et al.

(10) Patent No.: US 8,569,488 B2
(45) Date of Patent: Oct. 29, 2013

(54) CRYSTALLINE PYRIDAZINE COMPOUND

(75) Inventors: Eric D. Dowdy, Foster City, CA (US);
Kenneth M. Kent, Sunnyvale, CA (US);
Norma J. Tom, Belmont, CA (US);
Vahid Zia, San Carlos, CA (US)

(73) Assignees: Gilead Sciences, Inc., Foster City, CA (US); K.U. Leuven Research & Development, Leuven (BE); Gerhard Puerstinger, Igls (AT)

( * ) Notice: Subject to any disclaimer, the term of this patent is extended or adjusted under 35 U.S.C. 154(b) by 52 days.

(21) Appl. No.: 13/336,512

(22) Filed: Dec. 23, 2011

(65) Prior Publication Data

US 2012/0108601 A1 May 3, 2012

Related U.S. Application Data

(63) Continuation of application No. 12/217,347, filed on Jul. 3, 2008, now Pat. No. 8,106,054.

(60) Provisional application No. 60/958,595, filed on Jul. 6, 2007.

(51) Int. Cl.
*C07D 403/14* (2006.01)
*A61P 31/12* (2006.01)

(52) U.S. Cl.
USPC .......................................................... 544/238

(58) Field of Classification Search
USPC .......................................................... 544/238
See application file for complete search history.

(56) References Cited

U.S. PATENT DOCUMENTS

| | | | |
|---|---|---|---|
| 2,191,978 A | 2/1940 | Balle et al. |
| 2,411,662 A | 11/1946 | Martin et al. |
| 2,516,674 A | 7/1950 | Havertown et al. |
| 2,548,863 A | 4/1951 | Havertown et al. |
| 3,985,891 A | 10/1976 | Kutter et al. |
| 4,358,387 A | 11/1982 | Zoleski et al. |
| 4,565,816 A | 1/1986 | Neumann |
| 4,692,443 A | 9/1987 | Katner |
| 4,804,658 A | 2/1989 | Manley et al. |
| 4,914,108 A | 4/1990 | Khanna et al. |
| 4,988,707 A | 1/1991 | Stealey et al. |
| 4,990,518 A | 2/1991 | Khanna et al. |
| 5,011,832 A | 4/1991 | Dininno et al. |
| 5,019,581 A | 5/1991 | Khanna et al. |
| 5,057,517 A | 10/1991 | Johnston et al. |
| 5,137,896 A | 8/1992 | Van Daele |
| 5,208,242 A | 5/1993 | Khanna et al. |
| 5,227,384 A | 7/1993 | Khanna et al. |
| 5,302,601 A | 4/1994 | Khannal et al. |
| 5,332,744 A | 7/1994 | Chakravarty et al. |
| 5,374,638 A | 12/1994 | Dhanoa et al. |
| 5,405,964 A | 4/1995 | Mederski et al. |
| 5,438,063 A | 8/1995 | Osswald et al. |
| 5,446,032 A | 8/1995 | Whittaker et al. |
| 5,486,525 A | 1/1996 | Summers, Jr. et al. |
| 5,585,492 A | 12/1996 | Chandrakumar et al. |
| 5,587,372 A | 12/1996 | Aszodi et al. |
| 5,607,944 A | 3/1997 | Linz et al. |
| 5,719,306 A | 2/1998 | Chandrakumar et al. |
| 5,723,492 A | 3/1998 | Chandrakumar et al. |
| 5,854,265 A | 12/1998 | Anthony |
| 5,859,035 A | 1/1999 | Anthony et al. |
| 5,872,136 A | 2/1999 | Anthony et al. |
| 5,874,452 A | 2/1999 | Anthony |
| 5,880,140 A | 3/1999 | Anthony |
| 5,883,105 A | 3/1999 | Anthony |
| 5,939,557 A | 8/1999 | Anthony et al. |
| 6,051,574 A | 4/2000 | Anthony |
| 6,063,930 A | 5/2000 | Dinsmore et al. |
| 6,080,870 A | 6/2000 | Anthony et al. |
| 6,329,381 B1 | 12/2001 | Kurimoto et al. |
| 6,376,515 B2 | 4/2002 | Zhu et al. |
| 6,479,508 B1 | 11/2002 | Beaulieu et al. |
| 6,492,384 B1 | 12/2002 | Mederski et al. |
| 6,627,651 B1 | 9/2003 | Shiraishi |
| 6,767,654 B2 | 7/2004 | Tamao et al. |
| 6,770,666 B2 | 8/2004 | Hashimoto et al. |

(Continued)

FOREIGN PATENT DOCUMENTS

AU 643289 6/1991
CA 2093290 7/1993

(Continued)

OTHER PUBLICATIONS

Office Action for Chinese Patent Application No. 200880023677.X, mailed on Aug. 17, 2012.
Office Action for Colombian Patent Application No. 09-144.800, mailed on Sep. 7, 2012.
Office Action for Eurasian Patent Application No. 200900156, mailed on Sep. 11, 2012.
Office Action for Eurasian Patent Application No. 200971080, mailed on Sep. 6, 2012.
Office Action for European Patent Application No. 0882618808, mailed on Sep. 8, 2012.

(Continued)

*Primary Examiner* — James O Wilson
*Assistant Examiner* — Cecilia M Jaisle
(74) *Attorney, Agent, or Firm* — Clark + Elbing LLP

(57) ABSTRACT

A crystalline compound of formula (1) and its salts and solvates are provided for the treatment or prophylaxis of hepatitis C virus infections (1)

Methods of making and formulating crystalline compound (1) are provided.

19 Claims, 5 Drawing Sheets

(56) References Cited

U.S. PATENT DOCUMENTS

| | | | |
|---|---|---|---|
| 6,803,374 | B2 | 10/2004 | Priestley et al. |
| 6,835,739 | B2 | 12/2004 | Zhu et al. |
| 6,844,367 | B1 | 1/2005 | Zhu et al. |
| 7,026,051 | B2 | 4/2006 | Schauer et al. |
| 7,098,231 | B2 | 8/2006 | Poupart et al. |
| 7,112,600 | B1 | 9/2006 | Hashimoto et al. |
| 7,223,785 | B2 | 5/2007 | Beaulieu et al. |
| 7,285,551 | B2 | 10/2007 | Hashimoto et al. |
| 7,294,457 | B2 | 11/2007 | Kukolj et al. |
| 7,754,720 | B2 | 7/2010 | Bondy et al. |
| 7,956,184 | B2 | 6/2011 | Bondy et al. |
| 2003/0073836 | A1 | 4/2003 | Priepke et al. |
| 2003/0108862 | A1 | 6/2003 | Kukolj et al. |
| 2004/0082635 | A1 | 4/2004 | Hashimoto et al. |
| 2004/0097438 | A1 | 5/2004 | Hashimoto et al. |
| 2004/0097574 | A1 | 5/2004 | Marshall |
| 2004/0171626 | A1 | 9/2004 | Beaulieu et al. |
| 2004/0186125 | A1 | 9/2004 | Poupart et al. |
| 2005/0026921 | A1 | 2/2005 | Eckhardt et al. |
| 2005/0096337 | A1 | 5/2005 | Ackermann et al. |
| 2005/0222198 | A1 | 10/2005 | Bondy et al. |
| 2005/0239821 | A1 | 10/2005 | Neyts et al. |
| 2006/0052602 | A1 | 3/2006 | Kim et al. |
| 2006/0229336 | A1 | 10/2006 | Kazmierski et al. |
| 2006/0252791 | A1 | 11/2006 | Bondy et al. |
| 2007/0021472 | A1 | 1/2007 | Zhu et al. |
| 2007/0032497 | A1 | 2/2007 | Hashimoto et al. |
| 2007/0244148 | A1 | 10/2007 | Bondy et al. |
| 2008/0188516 | A1 | 8/2008 | Bondy et al. |
| 2008/0199427 | A1 | 8/2008 | Bondy |
| 2009/0036460 | A1 | 2/2009 | Dowdy et al. |
| 2010/0063059 | A1 | 3/2010 | Bondy |

FOREIGN PATENT DOCUMENTS

| | | |
|---|---|---|
| CA | 2158996 | 3/1994 |
| CA | 2357771 | 7/2000 |
| CA | 2471566 | 1/2003 |
| CA | 2423800 | 3/2003 |
| CA | 2496249 | 8/2003 |
| DE | 4122474 | 10/1993 |
| DE | 4230464 | 3/1994 |
| DE | 4236026 | 6/1994 |
| DE | 4309969 | 9/1994 |
| DE | 4318813 | 12/1994 |
| EP | 0076530 | 4/1983 |
| EP | 0138552 | 4/1985 |
| EP | 0228845 | 7/1987 |
| EP | 0232937 | 8/1987 |
| EP | 0300726 | 1/1989 |
| EP | 0344414 | 12/1989 |
| EP | 0417745 | 3/1991 |
| EP | 0462009 | 12/1991 |
| EP | 0510260 | 10/1992 |
| EP | 0605836 | 7/1994 |
| EP | 0706795 | 4/1996 |
| EP | 1132381 | 9/2001 |
| EP | 1162196 | 12/2001 |
| EP | 1386923 | 2/2004 |
| EP | 1400241 | 2/2004 |
| GB | 2158440 | 11/1985 |
| GB | 2264115 | 8/1993 |
| HU | 78019 | 5/1999 |
| IL | 89588 | 3/1989 |
| SU | 813921 | 12/1986 |
| SU | 1048742 | 12/1986 |
| SU | 851940 | 4/1988 |
| SU | 860463 | 5/1998 |
| WO | WO-92/22556 | 12/1992 |
| WO | WO-93/02080 | 2/1993 |
| WO | WO-93/14072 | 7/1993 |
| WO | WO-93/16075 | 8/1993 |
| WO | WO-94/12461 | 6/1994 |
| WO | WO-94/29321 | 12/1994 |
| WO | WO-95/02597 | 1/1995 |
| WO | WO-95/16687 | 6/1995 |
| WO | WO-96/11192 | 4/1996 |
| WO | WO-96/12703 | 5/1996 |
| WO | WO-96/15111 | 5/1996 |
| WO | WO-99/27929 | 6/1999 |
| WO | WO-00/20400 | 4/2000 |
| WO | WO-00/20416 | 4/2000 |
| WO | WO-00/20425 | 4/2000 |
| WO | WO-00/20445 | 4/2000 |
| WO | WO-00/39127 | 7/2000 |
| WO | WO-00/40583 | 7/2000 |
| WO | WO-00/40586 | 7/2000 |
| WO | WO-00/73307 | 12/2000 |
| WO | WO-01/60315 | 8/2001 |
| WO | WO-01/66526 | 9/2001 |
| WO | WO-01/85172 | 11/2001 |
| WO | WO-01/95910 | 12/2001 |
| WO | WO-02/04425 | 1/2002 |
| WO | WO-02/057425 | 7/2002 |
| WO | WO-02/067942 | 9/2002 |
| WO | WO-03/000254 | 1/2003 |
| WO | WO-03/004020 | 1/2003 |
| WO | WO-03/007945 | 1/2003 |
| WO | WO-03/010140 | 2/2003 |
| WO | WO-03/010141 | 2/2003 |
| WO | WO-03/014229 | 2/2003 |
| WO | WO-03/026587 | 4/2003 |
| WO | WO-03/057205 | 7/2003 |
| WO | WO-2004/005286 | 1/2004 |
| WO | WO-2004/018468 | 3/2004 |
| WO | WO-2004/019935 | 3/2004 |
| WO | WO-2004/033455 | 4/2004 |
| WO | WO-2004/043913 | 5/2004 |
| WO | WO-2004/054974 | 7/2004 |
| WO | WO-2004/067516 | 8/2004 |
| WO | WO-2004/072243 | 8/2004 |
| WO | WO-2005/063744 | 7/2005 |
| WO | WO-2006/029966 | 3/2006 |
| WO | WO-2006/033703 | 3/2006 |
| WO | WO-2006/069193 | 6/2006 |
| WO | WO-2007/063744 | 6/2007 |
| WO | WO-2008/005519 | 1/2008 |
| WO | WO-2009/009001 | 1/2009 |

OTHER PUBLICATIONS

Office Action for Australian Patent Application No. 2011253901, mailed on Aug. 15, 2012.

Office Action for Japanese Patent Application No. 2010-514874, mailed on Nov. 19, 2012.

World Health Organization, Hepatitis C, Surveillance and Control, http://www.who.int/csr/disease/hepatitis/whocdscsrlyo2003/en/index4.html, downloaded Sep. 30, 2009.

U.S. Appl. No. 11/658,625, filed Jul. 26, 2005, Kim et al.

Akamatsu et al., "New Efficient Route for Solid-Phase Synthesis of Benzimidazole Derivatives," *J. Comb. Chem.* 4:475-483 (2002).

Baba et al., "Synergistic Antiviral Effects of Antiheroes Compounds and Human Leukocyte Interferon on Varicella-Zoster Virus *in Vitro*," *Antimicrobial Agents Chemother.* 25:515.517, 1984.

Baginski et al., "Mechanism of Action of a Pestivirus Antiviral Compound," *Proc. Natl. Acad. Sci. U.S.A.* 97:7981-7986, 2000.

Barlin and Fenn, "A Carbon-13 Nuclear Magnetic Resonance Study of Protonation in Imidazo[4,5-c]pyridines," *Aust. J. Chem.* 34:1341-1344 (1981).

Barlin and Fenn, "The Preparation and 1H NMR Spectra of Some N-Methylpurines and Related Compounds," *Aust. J. Chem.* 36:633-638 (1983).

Barlin, "Ionisation Constants of Heterocyclic Substances, Part VIII. 1,3,5-Triazindenes,"*J. Chem. Soc. B: Phys.Org.* 4:285-291, 1966.

Barraclough et al., "An Adventitious Synthesis of a 5-Methylimidazo[4,5-c]pyridine Derivative," *Tet. Lett.* 27:5997-6000 (1986).

Barraclough et al., "Inotropic "A" Ring Substituted Sulmazole and Isomazole Analogues," *J. Med. Chem.* 33:2231-2239 (1990).

Brown et al., "Purine Analogues as Amplifiers of Phleomycin. V. Thioethers of Several Heterocyclic Systems with One or Two Rings," *Aust. J. Chem.* 32:2713:2726 (1979).

(56) References Cited

OTHER PUBLICATIONS

Chou et al., "Quantitative Analysis of Dose-Effect Relationships: The Combined Effects of Multiple Drugs or Enzyme Inhibitors," *Adv. Enzyme Reg.* 22:27-55, 1984.
Cleve et al., "Derivates des Imidazo[4,5-b]- und Imidazo[4,5-c]-Pyridins," *Liebigs Ann. Chem.* 747:158-171, 1971 (and translation).
Curtin et al., "Discovery and Evaluation of a Series of 3-Acylindole Imidazopyridine Platelet-Activating Factor Anatagonists," *J. Med. Chem.* 41:74.95 (1998).
Elion et al., "Antagonists of Nucleic Acid Derivatives. VIII. Synergism in Combinations of Biochemically Related Antimetabolites," *J. Biol. Chem.* 208:477-488, 1954.
Final Rejection, Dec. 16, 2008, U.S. Appl. No. 11/019,830.
Final Rejection, Mar. 19, 2007, U.S. Appl. No. 11/316,050.
Fletcher et al., "Heterocyclic Systems," *Nomenclature of Organic Adv. Ser.* pp. 49-64, 1974.
Grazul et al. Natural Product Letters (1994) 5(3):187-195.
Greenfield et al., "Increase in the Stability and Helical Content of Estrogen Receptor Alpha in the Presence of the Estrogen Response Element: Analysis by Circular Dichroism Spectroscopy," *Biochemistry* 40:6646-6652, 2001.
Griesser, Chapter 8, The Importance of Solvates (pp. 211-230), in the text, Polymorphism: In the Pharmaceutical Industry, Hilfiker, 2006.
Guillory (in Britain ed.) "Polymorphism etc." NY:marcel Dekker Inc. 1999, 1-2, 183-226.
International Preliminary Examination Report (PCT/BE03/00117) (mailed Sep. 3, 2004).
International Preliminary Report on Patentability for PCT/US2004/043112 dated Apr. 25, 2006.
International Preliminary Report on Patentability for PCT/US2005/026606 dated Feb. 20, 2007.
International Preliminary Report on Patentability for PCT/US2005/046477 dated Mar. 16, 2007.
International Preliminary Report on Patentability for PCT/US2007/015553 dated Jan. 13, 2009.
International Search Report for PCT/BE2003/000117 dated Dec. 16, 2003.
International Search Report for PCT/US2004/043112 dated Jun. 27, 2005.
International Search Report for PCT/US2005/026606 dated Feb. 13, 2006.
International Search Report for PCT/US2005/046477 dated Jun. 2, 2006.
International Search Report for PCT/US2007/015553 dated Mar. 6, 2008.
International Search Report for PCT/US2008/008259 dated Oct. 14, 2008.
Jacob III, P., "Resolution of (+/−) 5-Bromonornicotine. Sythesis of (R)- and (S)- Nornicotine of High Enantiomeric Purity," *J. Org. Chem.* 47:4165-4167, 1982.
Johnson, A.W. Invitation to Organic Chemistry 1999 Jones and Bartlett: Missisauga, Canada p. 24.
Jones, Maitland Organic Chemistry Norton: New York, 1997, p. 84-99.
Kariv et al., "Improvement of 'Hit-to-Lead' Optimization by Integration of in Vitro HTS Experimental Models for Early Determination of Pharmacokinetic Properties," *Comb. Chem. High Throughput Screen.* 5:459-472, 2002.
Kiyama et al., "Synthesis and Evaluation of Novel Nonpeptide Angiotesin II Receptor Antagonists: Imidazo[4,5-c]pyridine Derivatives with an Aromatic Substiluent," *Chem, Pharm. Bull.* 43:450-460 (1995).
Kuno et al (1993) "Studies on Cerebral Protective Agents, IV. Synthesis of Novel 4-Arylpyridine and 4-arylpyridazine Derivatives with Anti-Anoxic Activity," Chem Phar. Bull. 41(1):136-162.
Lindenbach et al. (2005) "Unraveling Hepatitis C Virus Replication from Genome to Function," Nature 436-:933-938.

Lochmüller et al., "Chromatographic Resolution of Enantiomers Selective Review," *J. Chromatography* 113:283-302, 1975.
Mederski and Pachter, "Synthesis and Structural Assignment of Some N-Substituted Imidazopyridine Derivatives," *Tetrahedron* 48:10549-10558 (1992).
Montgomery et al., "1-B-D-Arabinofuranosyl, etc.," J. Med. Chem., 1982,25,96-98.
Non-Final Rejection, Dec. 12, 2008, U.S. Appl. No. 10/519,756.
Non-Final Rejection, Feb. 11, 2009, U.S. Appl. No. 10/583,814.
Non-Final Rejection, Mar. 12, 2008, U.S. Appl. No. 11/019,830.
Non-Final Rejection, Mar. 25, 2009, U.S. Appl. No. 12/022,557.
Non-Final Rejection, Oct. 29, 2008, U.S. Appl. No. 11/825,598.
Non-Final Rejection, Sep. 27, 2006, U.S. Appl. No. 11/316,050.
Okamoto et al., "Optical Resolution of Dihydropyridine Enantiomers by High-Performance Liquid Chromatography Using PhenylCarbamates of Polysaccharides as a Chiral Stationary Phase," *J. Chromatography* 513:375-378, 1990.
Paeshuyse et al., "A Novel, Highly Selective, etc.," J of Virology, Jan. 2006, 80(1), 149-160.
Penning et al., "Synthesis of Imidazopyridines as Potent Inhibitors of Leukotriene A4 Hydrolase," *Bioorg. Med. Chem. Lett.* 13:1137-1139, 2003.
Puerstinger et al. "Substituted 5-benzyl-2-phenyl-5H-imidazo[4,5-c]pyridines: A new class of pestivirus inhibitors" Bioorganic & Medicinal Chemistry Letters 2006, 16:5345-5349.
Puertstinger et al. "Antiviral 2,5-disubstituted imidazo[4,5-c]pyridines: From anti-pestivirus to anti-hepatitis C virus activity" Bioorganic & Medicinal Chemistry Letters 2007, 17:391-393.
Rigaudy et al., "Fundamental Heterocyclic Systems," *Nomenclature of Organic Adv. Ser.* pp. 53-76, 1979.
Robertson et al., "Structure-Activity Relationships of Arylimidazopyridine Cardiotonics: Discovery and Inotropic Activity of 2-[2-Methoxy-4-(methylsulfinyl)phenyl]-1*H*-imidazo[4,5-c]pyridine," *J. Med. Chem.* 28:717-727 (1985).
Savarino et al., "Spectral Behaviour of Linked Heterocyclic Systems and Related Dyes," *Spectrochim. Acta A: Mol. Blomol. Spectrosc.* 49A:1379-1393 (1993).
Self et al. (1991) "Romzarit: A Potential Disease-Modifying Antirheumatic Drug," J. Med. Chem. 34:772-777.
Siddiqui et al., "3-Deaza- and, etc.," J. Med. Chem., 1995, 38, 1035-1038.
Stanovnik et al., "Methylation of Heterocyclic Compounds Containing NH, SH, and/or OH Groups by Means of N,N-Dimethylformamide Dimethyl Acetal," *Aust. J. Chem.* 34:1729-1738 (1981).
Vassilev et al., "Authentic and Chimeric Full-Length Genomic cDNA Clones of Bovine Viral Diarrhea Virus that Yield Infectious Transcripts," *J. Virol.* 71:471-478 (1997).
Vippagunta et al. "Crystalline Solid," Advanced Drug Delivery Reviews 48:3-26 (2001).
Wang et al., Non-Nucleoside Analogue Inhibitors Bind to an Allosteric Sile on HCV NS5B Polymerase. Crystal Structures and Mechanism of Inhibition: *J. Biol. Chem.* 278:9489-9495 (2003).
Written Opinion for PCT/US2004/043112 dated Oct. 18, 2005.
Written Opinion for PCT/US2005/046477 dated Jun. 2, 2006.
Written Opinion for PCT/US2007/015553 dated Jan. 7, 2009.
Written Opinion for PCT/US2005/026606 dated Feb. 13, 2006.
Yutilov et al., Synthesis and Antiviral Activity of Spinaceamine: *Khim. Farm. Zh.* 23:56-59 (1989) (and translation).
Zhana, "Inhibitors of Hepatitis C—A Review of the Recent Patent Literature," *Drugs* 5:154-158 (2002).
Zhang, "Studies on the Synthesis and Single Crystal Structure of 3-methyl-6-(p-methylphenyl) Pyridazine," 2001 Journal of Sichuan Normal University (Natural Science) 24(4):384-386 (and translation).
Office Action for Eurasian Patent Application No. 200971080/28, dated May 24, 2011.
World Health Organization, Hepatitis C, Surveillance and Control, http://www.who.int/csr/disease/hepatitis/whocdscsrlyo2003/en/index4.html, 2002.

Figure 4 DSC

CRYSTALLINE PYRIDAZINE COMPOUND

CROSS-REFERENCE TO RELATED APPLICATIONS

This application claims priority to U.S. Provisional Application Ser. No. 60/958,595 entitled "Crystalline Pyridazine Compound and Use Thereof," filed Jul. 6, 2007. The content of this provisional application is herein incorporated by reference in its entirely for all purposes.

BACKGROUND OF THE INVENTION

The hepatitis C virus is an enveloped, single-stranded, positive sense RNA virus in the family Flaviviridae. HCV mainly replicates within hepatocytes in the liver. Circulating HCV particles bind to receptors on the surfaces of hepatocytes and subsequently enter the cells. Once inside the hepatocyte, HCV utilizes the intracellular machinery necessary to accomplish its own replication. Lindenbach, B. Nature 436 (7053):932-8 (2005). The HCV genome is translated to produce a single protein of around 3011 amino acids. This "polyprotein" is then proteolytically processed by viral and cellular proteases to produce three structural (virion-associated) and seven nonstructural (NS) proteins.

HCV encodes two proteases, the NS2 cysteine autoprotease and the NS3-4A serine protease. The NS proteins then recruit the viral genome into an RNA replication complex, which is associated with rearranged cytoplasmic membranes. RNA replication takes places via the viral RNA-dependent RNA polymerase of NS5B, which produces a negative-strand RNA intermediate. The negative strand RNA then serves as a template for the production of new positive-strand viral genomes. Nascent genomes can then be translated, further replicated, or packaged within new virus particles. New virus particles presumably bud into the secretory pathway and are released at the cell surface.

HCV has a high rate of replication with approximately one trillion particles produced each day in an infected individual. Due to lack of proofreading by the HCV RNA polymerase, HCV also has an exceptionally high mutation rate, a factor that may help it elude the host's immune response.

Based on genetic differences between HCV isolates, the hepatitis C virus species is classified into six genotypes (1-6) with several subtypes within each genotype. Subtypes are further broken down into quasispecies based on their genetic diversity. The preponderance and distribution of HCV genotypes varies globally. For example, in North America genotype 1a predominates followed by 1, 2a, 2b, and 3a. In Europe genotype 1 is predominant followed by 2a, 2b, 2c, and 3a. Genotypes 4 and 5 are found almost exclusively in Africa. Genotype is clinically important in determining potential response to interferon-based therapy and the required duration of such therapy. Genotypes 1 and 4 are less responsive to interferon-based treatment than are the other genotypes (2, 3, 5 and 6). Duration of standard interferon-based therapy for genotypes 1 and 4 is 48 weeks, whereas treatment for genotypes 2 and 3 is completed in 24 weeks.

The World Health Organization estimates that world-wide 170-200 million people (3% of the world's population) are chronically infected with HCV. Approximately 75% of these individuals are chronically infected with detectable HCV RNA in their plasma. These chronic carriers are at risk of developing cirrhosis and/or liver cancer. In studies with a 7-16 years follow-up, 7-16% of the patients developed cirrhosis, 0.7-1.3% developed hepatocellular carcinoma and 1.3-3.7% died of liver-related disease.

The only treatment option available today is the use of interferon α-2 (or its pegylated form) either alone or combined with ribavirin. However, sustained response is only observed in about 40% of the patients and treatment is associated with serious adverse effects. There is thus an urgent need for potent and selective inhibitors of HCV.

Relevant disclosures include U.S. Pat. Nos. 4,914,108; 4,988,707; 4,990,518; 5,137,896; 5,208,242; 5,227,384; 5,302,601; 5,374,638; 5,405,964; 5,438,063; 5,486,525; 6,479,508; and U.S. Patent Publication No. US2003/0108862 A1, Canadian Patent No. 2423800 A1, German Patent Nos. 4211474 A1, 4236026, 4309969, 4318813, European Patent Nos. EP 0 138 552 A2, EP 0 706 795 A2, EP 1 132 381 A1, Great Britain Patent No. 2158440 A, PCT Patent Publication Nos. WO 00/20416, WO 00/39127, WO 00/40583, WO 03/007945 A1, WO 03/010140 A2, WO 03/010141 A2, WO 93/02080, WO 93/14072, WO 96/11192, WO 96/12703, WO 99/27929, PCT-US2004/43112, PCT-BE2003/000117, PCT-US2005/26606, Akamatsu, et al., "New Efficient Route for Solid-Phase Synthesis of Benzimidazole Derivatives", 4:475-483, *J. COMB. CHEM.*, 2002, Baginski S G et al., Proc. Natl. Acad. Sci. U.S.A. 2000 Jul. 5; 97(14):7981-6). Cleve et al., "Derivate des Imidazo[4.5-b]- and Imidazo[4.5-c]pyridins", 747:158-171, *JUSTUS LIEBIGS ANNALEN DER CHEMICA,* 1971, Kiyama, et al., "Synthesis and Evaluation of Novel Nonpeptide Angiotensin II Receptor Antagonists: Imidazo[4,5-c]pyridine Derivatives with an Aromatic Substituent", 43(3):450-60, *CHEM PHARM BULL,* 1995, Mederski et al., "Synthesis and Structural Assignment of Some N-substituted Imidazopyridine Derivatives", 48(48): 10549-58, *TETRAHEDRON,* 1992, Yutilov et al., 23(1):56-9, *KHIMIKO-FARMATSEVTICHESKII ZHURNAL,* 1989. In addition, see WO 05/063744.

The compound of formula (1) is the subject of WO 08/005,519.

(1)

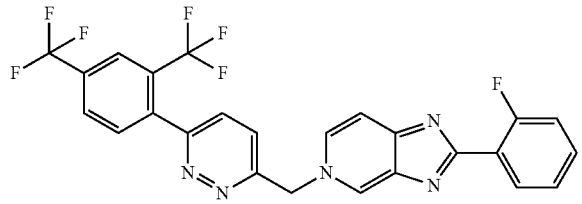

Compound (1) as produced by the process of WO 05/063744 is substantially or entirely amorphous. It is believed to be a hydrate (hereafter "amorphous" compound (1)).

It is an object of this invention to provide compound (1) in crystalline form.

SUMMARY OF THE INVENTION

In accordance with achieving the foregoing objects of this invention, a crystalline compound is provided having formula (1)

(1)

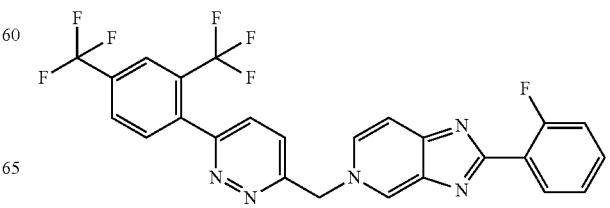

and its salts, which is substantially free of amorphous compound (1).

In an embodiment, the crystalline compound (1) is the free base substantially free of amorphous compound (1) and any other crystal form of compound (1).

Another embodiment of this invention is a method for making crystalline compound (1)

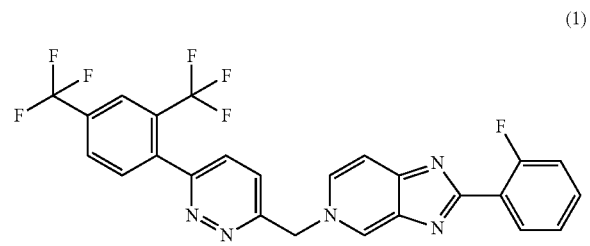 [SMILES: Fc1ccccc1-c1nc2ccn(Cc3ccc(-c4ccc(C(F)(F)F)cc4C(F)(F)F)nn3)cc-2n1]

(1)

comprising crystallizing compound (1) from crystallization solvent and controlling the amount of water in the crystallization solvent.

In another embodiment, a composition is provided that comprises crystalline free base compound (1) which is substantially free of the chloride salt of compound (1).

Crystalline compound (1) is useful in a method for therapy or prophylaxis of HCV infection comprising administering to a subject a therapeutic or prophylactic dose of crystalline compound (1). Another embodiment comprises the use of crystalline compound (1) for the manufacture of a medicament for the prevention or treatment of an HCV infection in a mammal (more specifically a human).

Another embodiment of this invention relates to pharmaceutical compositions of the crystalline formula (1) compound comprising at least one pharmaceutically acceptable excipient. In one embodiment the compound of formula (1) is formulated with an organic acid and optionally formulated into a pharmaceutical dosage form such as a capsule. In another embodiment, crystalline compound (1) is micronized and formulated as a suspension.

Crystalline compound (1) or the pharmaceutical compositions of this invention are employed in the treatment or prophylaxis of hepatitis C.

Crystalline compound (1) exhibits improvements in pharmacological features and cost advantages, in particular improved purity, storage stability and manufacturing reproducibility. A particular advantage is its higher melting point as compared to the amorphous form.

Other features of this invention, including novel intermediates and product compositions, will be apparent from consideration of this application as a whole.

FIGURES

DETAILED DESCRIPTION OF THE INVENTION

Crystalline compound (1) is defined as a solid comprising compound (1) in which the constituent molecules are packed in a regularly ordered repeating pattern extending in all three spatial dimensions. Identification of crystallinity is readily accomplished in a number of ways known to those skilled in the art. Microscopic examination of the test composition often will reveal the presence of regular shapes, suggesting ordered internal structure. In the case of the crystal embodiment produced in example 1, the regular shape generally is rod or needle-like.

Figure 1:
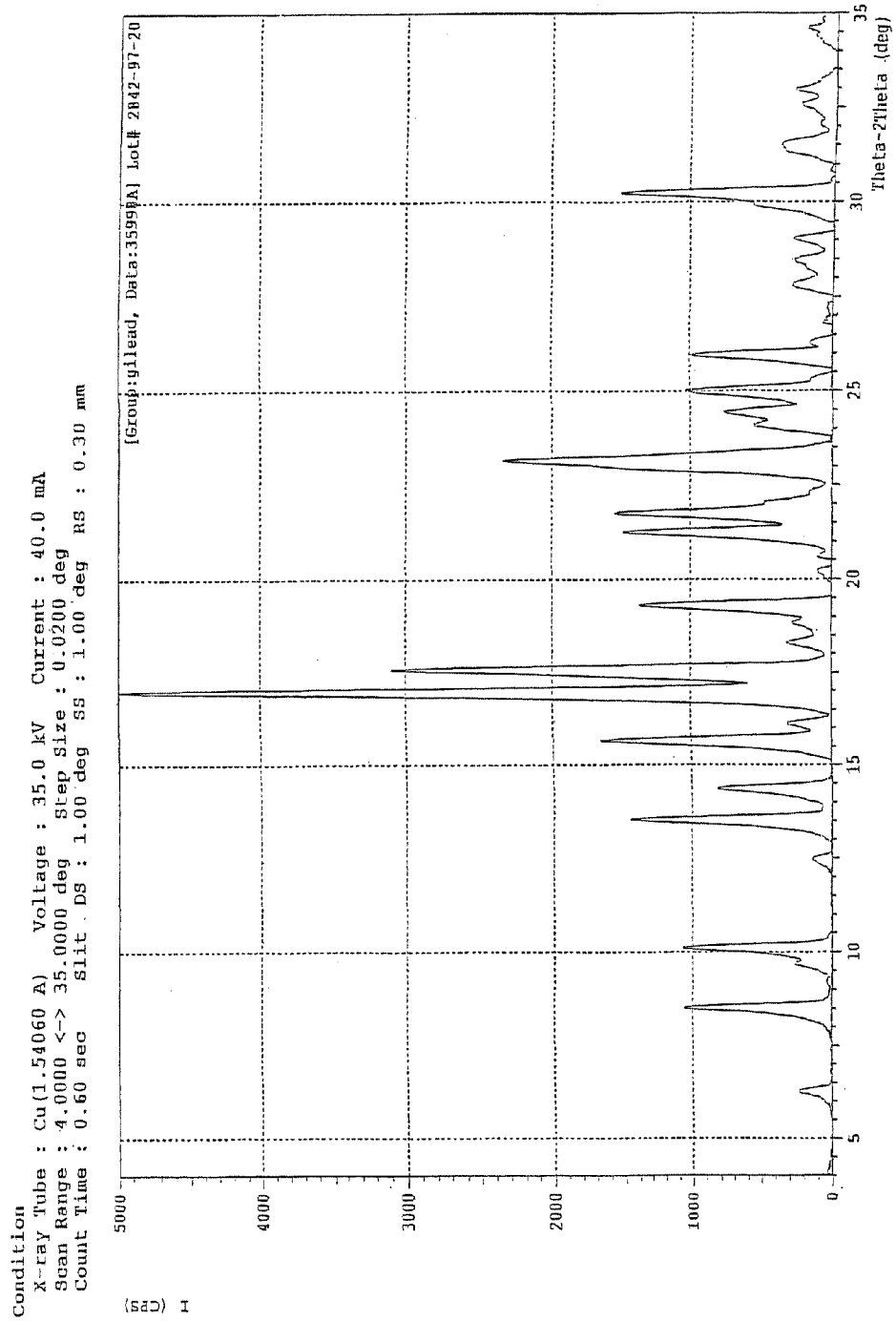
FIG. 1 depicts an X-ray powder diffraction (XRPD) pattern obtained for crystalline compound (1) reference standard obtained by the method of example 1.
Figure 2:
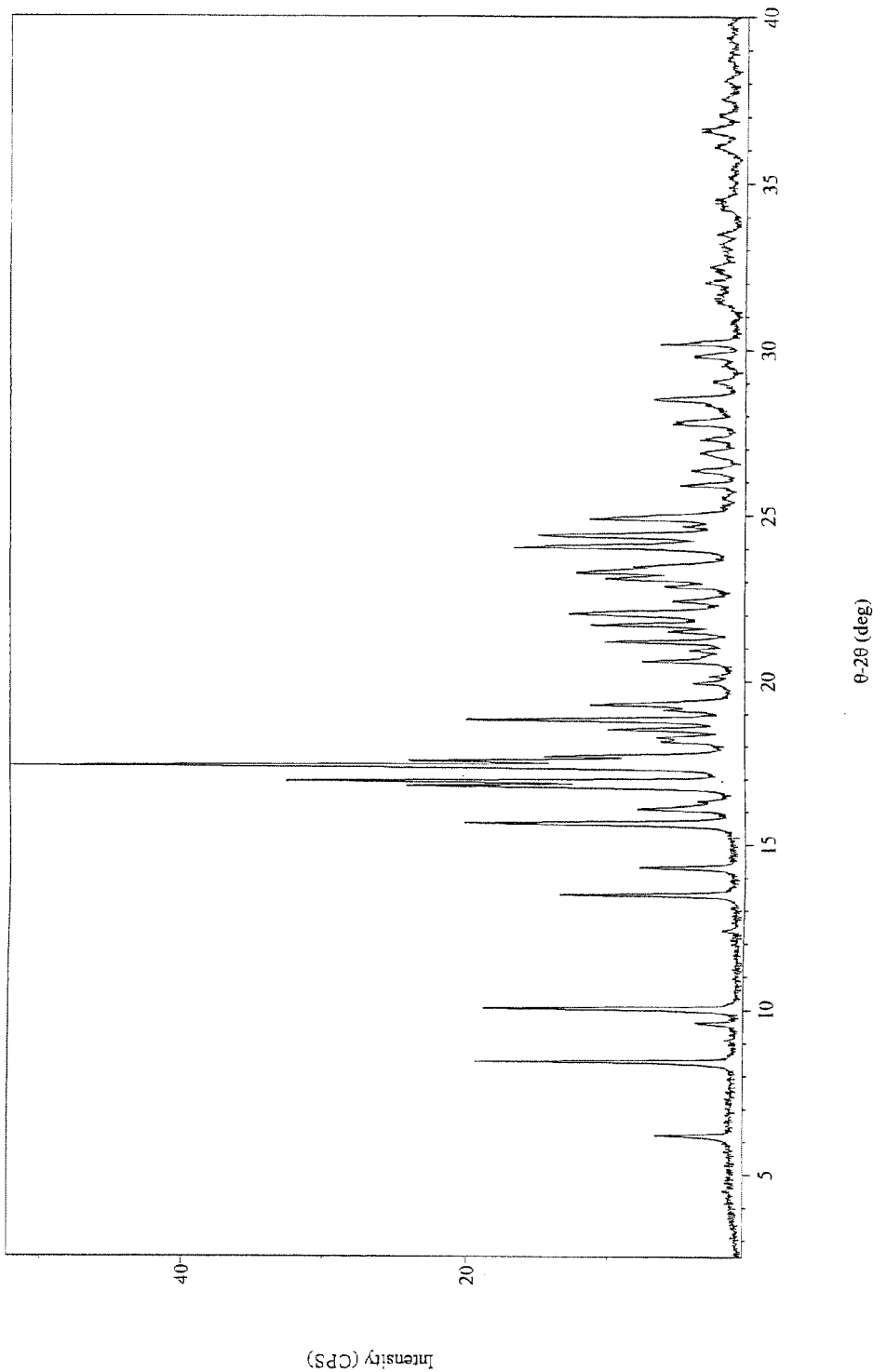
FIG. 2 depicts another X-ray powder diffraction pattern obtained for crystalline compound (1).
Figure 3:
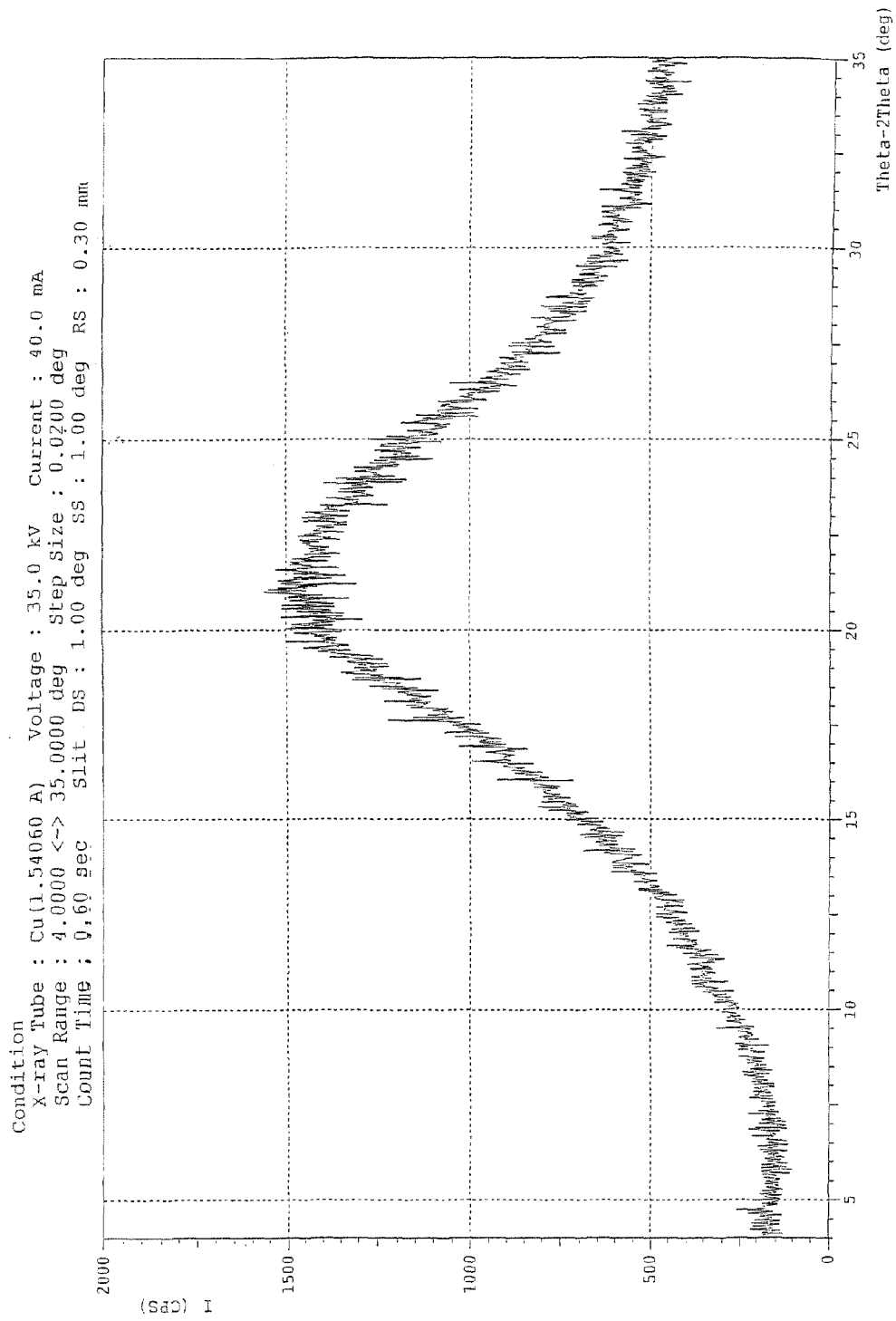
FIG. 3 is an X-ray powder diffraction pattern obtained for the amorphous form of compound (1) Research Lot 6, obtained by the method of Example 1a in WO 08/005519.

XRPD is another method for identifying crystalline compound (1). The regularly ordered structure of constituent molecules in a crystal diffracts incident x-rays in a distinct pattern depicted as a spectrum of peaks. This pattern of peaks for crystalline compound (1) is shown in FIGS. 1 and 2. On the other hand, FIG. 3 depicts an XRPD for substantially amorphous compound (1), which lacks distinct peaks. While the XRPD peaks for crystalline compound (1) may vary in intensity the same general pattern will be present in replicate x-ray diffraction analysis.

Crystalline compound (1) exhibits an XRPD dominant peak(s) at about 17 degrees theta 2θ, ordinarily 17.4 and 17.5. By "about" applicants mean within the typical variation in measurement of XRDP peaks. Such variations may result from the use of different instruments, instrument settings, batches of product, post-crystallization processing such as micronization or milling, and with varying sample preparation methods. In general, "about" means±0.5 degree theta 2θ. An example of this sort of variation can be seen by comparing FIGS. 1 and 2. In particular, peak intensity (e.g., at about 30) may vary due to crystal orientation effects.

Illustrative examples of other dominant peaks for crystalline compound (1) are at about 8, 10, 13, 16, 19 and 24 degrees theta 2θ, ordinarily 8.4, 10.0, 13.5, 15.7, 16.8, 16.9, 18.8 and 24.4. Any one or more of these peaks (but especially, 8, 10, 15.7, 16.7 and 16.9, with or without the peaks at about 17, are suitably employed to define the XRDP for crystalline compound (1).

The identification of a crystal form of compound (1) need not require the presence of any one or more of the dominant peaks seen in FIG. 1 or 2. Rather, the presence or absence of dominant peaks ordinarily is taken into account with other diagnostic characteristics (e.g., DSC thermogram) to identify a candidate as crystalline compound (1).

Crystalline compound (1) also is characterized by DSC thermogram, which reveals an endothermic onset at about 235° C. in differential scanning calorimetry profile. Typically, some variation in this measurement also will be encountered (usually, ±1-3° C.).

Crystalline compound (1) also is characterized by its heat of fusion ($DH_f$) of about 81 J/g (42 KJ/mole).

Crystalline compound (1) is made by a process comprising dissolving compound (1) in solvent and forming crystals therefrom. Typical solvents for use herein are ethyl acetate, isopropyl alcohol or a cosolvent containing ethyl acetate and isopropyl alcohol. Other suitable solvents are obtained from the solubility map in McConville, F. X. "Pilot Plant Real Book" (2002) which plots the dielectric constant and Hildebrand solubility parameter for a variety of solvents.

Solvents close to ethyl alcohol and isopropyl alcohol on the map (dielectric 2.5-20 and Hildebrand 15-24) are ethyl ether, isobutyl acetate, butyl acetate, anisole, chlorobenzene, chloroform, methyl acetate, THF, dichloromethane, dichloroethane, 1,2-dichlorobenzeke, methylisobutylketone, methylethylketone, cyclohexanone, acetone, 1-butanol, 2-methoxyethanol, isobutanol, 2-butanol, cyclohexanol, isoamyl alcohol, pyridine, methyl formate, 1-pentanol, and/or 2-butoxyethanol.

Some of these solvents would not be preferred due to toxicity issues, but this could be overcome by careful solvent removal from the product. It will be within the skill of the ordinary artisan to conduct laboratory screening to determine suitability of a candidate solvent for the preparation of crystalline compound (1). Combinations of these solvents also fall within the scope of the invention.

A key finding facilitating the preparation of crystalline compound (1) is that the water content of the crystallization solvent must be controlled in order to obtain and/or optimize the production of crystalline product. For example, when using ethyl acetate as solvent, the upper limit on water content is about 0.6% to 0.9% by weight.

An additional consideration with regard to water content is its use to remove other forms of compound (1) that are less soluble than the crystalline free base in liquid lipophilic pharmaceutical carriers. For example the chloride salt of compound (1) is less soluble than the free base in the fatty acid solutions employed as carriers herein. In sufficiently large amounts such salts produce an undesirable haze in the pharmaceutical product. The final synthetic step of example 1 produces a mixture of free base together with minor amounts of the chloride salt. The haze-producing chloride salt is removed by first dissolving the product in a solvent containing a relatively high amount of water (about 3%-10%) at alkaline pH. Refluxing in this solvent assures that there is enough water to back convert the chloride salt to the free base. Thereafter, the crystalline free base is crystallized from this solvent. This process optionally is repeated with decreasing water concentrations to gradually remove the chloride salt from the product. The final step is then accomplished with low water content (usually less than about 0.9% water) in order to crystallize the free base substantially free of the amorphous compound (1). In general, haze in the pharmaceutical preparation is not encountered when the chloride content in the final product is ordinarily less than about 100 ppm. The amounts of water employed will vary depending upon the concentration of contaminating chloride salt and other experimental variables determinable by the skilled artisan. In summary, the water content of the crystallization solvent is controlled, both to convert chloride (or other relatively water soluble salts of compound (1)) and to avoid generation of amorphous compound (1).

The amount of permitted water for each function will vary depending upon the solvent or solvents employed for crystallization, the concentration of compound (1), the temperature of the crystallization step, the time of crystallization, the tolerable amount of amorphous compound (1), and other variables. Hence, it will be incumbent upon the artisan to determine the optimal water level for obtaining the desired results, usually by conducting a typical variable matrix study. The lowest water concentration for avoiding generation of the amorphous compound (1) is more a matter of practical economics. For example, 0.05% water by weight is acceptable.

In general, the final crystallization step is conducted in substantially anhydrous solvent. Substantially anhydrous solvent is defined as solvent containing a sufficiently small amount of water that the resulting product contains crystalline compound (1) and is substantially free of amorphous compound (1), typically less than about 40%, ordinarily less than about 30, 20, 10, 5, 3, 2 or 1% by weight of amorphous compound (1) in the total of all forms of compound (1) in the product composition.

In general, substantially anhydrous solvent will about 0.5%-0.9% water by weight of the crystallization solvent. However, more water can be present if the desired product is permitted to contain the greater proportions of amorphous compound (1). However, it is optimal if the compound (1) composition is free of detectable amorphous compound (1).

The water content is controlled by any manner results in the proper amount of water in the crystallization step concerned. When formation of amorphous compound (1) is to be avoided, suitable techniques for minimizing or reducing the amount of water include adding drying agents and/or azeotropically removing water. It is most convenient to remove water during reflux dissolution of compound (1) just prior to crystallization. Of course, control of water content includes adding water as well, as will typically be the case during steps to convert the chloride salt.

Amorphous compound (1) optionally is used as starting material for crystallization (form conversion). Alternatively, crystallization is conducted directly from the final reaction products without an intermediate recovery of amorphous compound (1). The crystallization typically is conducted by providing or dissolving compound (1) in solvent or solvent mixture at reflux (sufficient to dissolve compound (1), about 1 to 5 hours), followed by cooling to about 18-23° C. over 4-8 hours, then optionally agitated for about 8 to 20 hours at about 18-23° C. Agitation is optional but increases the rate of crystallization. Reflux is not critical since all that is necessary is that compound (1) be placed in solution. However, refluxing compound (1) has the advantage of rapidly dissolving compound (1) and azeotropically removing water at the same time. Water is controlled before crystallization starts or during crystallization, or both, although in general it is best to reduce water below the desired limit before any compound (1) can precipitate as the amorphous polymorph.

Generation of amorphous material is optimized by using relatively longer crystallization times, higher temperatures and lower concentrations of compound (1). Determining the various optimal crystallization process parameters are well within the skill of the ordinary artisan.

An embodiment herein is a composition made by the process of combining crystalline compound (1) with a pharmaceutically acceptable excipient and forming a pharmaceutical dosage form such as a tablet or capsule. The resulting product need not contain crystalline compound (1). While it is expected that dosage forms made from crystalline compound (1) will contain only compound (1) in crystalline form. However, in some embodiments the crystalline compound (1) is an intermediate for dissolution in the carrier or excipient.

The crystalline compound (1) of this invention is administered to a subject mammal (including a human) by any means well known in the art, i.e. orally, intranasally, subcutaneously, intramuscularly, intradermally, intravenously, intra-arterially, parenterally or by catheterization in a therapeutically effective amount, i.e., an HCV-inhibiting amount or an HCV-replication inhibiting amount. This amount is believed to be an amount that ensures a plasma level of about 100 nM, 3 times the protein-adjusted EC90. This ordinarily is expected to be achieved by daily oral administration of about 0.5—about 5 mg/kg, typically about 0.7 to 2.2 mg/kg, most ordinarily about 1.2 mg/kg bodyweight for humans.

The optimal dosage of the compound of this invention will depend upon many factors known to the artisan, including bioavailability of the compound in a given formulation, the metabolism and distribution of the compound in the subject, the fasted or fed state of the subject, selection of carriers and excipients in the formulation, and other factors. Proper dosing typically is determined in the preclinical and clinical settings, and is well within the skill of the ordinary artisan. The therapeutically effective amount of the compound of this invention optionally is divided into several sub-units per day or is administered daily or in more than one day intervals, depending upon the nature of the infection, the patient's general condition and the formulation of the compound of this invention. Generally, the compound is administered twice daily.

The compound of this invention is employed in concert with other agents effective against HCV infections. They optionally are administered separately in a course of therapy, or are combined with compound (1) in a unitary dosage form such as tablet, iv solution or capsule. Such other agents include, for instance, interferon-alpha, ribavirin, and/or compounds falling within the disclosures of EP1162196, WO 03/010141, WO 03/007945, WO 00/204425 and/or WO 03/010140 (and other filings within their patent families). Other agents for administration in a course of therapy with the compound of this invention include compounds now in clinical trials, in particular HCV protease inhibitors such as VX-950 (Vertex Pharmaceuticals), SCH 5030347 (Schering Plough) and BILN-2061 (Boehringer Ingelheim), nucleoside HCV inhibitors such as NM283, NM107 (both Idenix/Novartis) and R1626 (Hoffmann-LaRoche), and non-nucleoside HCV inhibitors including HCV-086 and -796 (both ViroPharma/Wyeth). Supplementary antiviral agents are used in conventional amounts. If the efficacy of the compound of this invention and the supplementary compound are additive then the amounts of each active agent optionally are commensurately reduced, and more so if the agents act synergistically. In general, however, the agents are used in their ordinary active amounts in unitary combination compositions.

Co-administered agents generally are formulated into unitary compositions with the compound of this invention so long as they are chemically compatible and are intended to be administered by the same route. If not, then they optionally are provided in the form of a medical kit or package containing the two agents in separate repositories or compartments.

The compound of this invention typically is provided as the free base, but also optionally is prepared as a salt. Salts typically are prepared by acid addition of organic and/or inorganic acids to the free base. Examples include (1) inorganic acids such as hydrohalogen acids, e.g. hydrochloric or hydrobromic acid, sulfuric acid, nitric acid, phosphoric acid and sulfamic acids; or (2) organic acids such as acetic, propanoic, hydroxyacetic, benzoic, 2-hydroxypropanoic, 2-oxopropanoic, lactic, fumaric, tartaric, pyruvic, maleic, malonic, malic, salicylic (e.g. 2-hydroxybenzoic), p-aminosalicylic, isethionic, lactobionic, succinic, oxalic and citric acids; organic sulfonic acids, such as methanesulfonic, ethanesulfonic, benzenesulfonic, p-toluenesulfonic, C1-C6 alkylsulfonic, benzenesulfonic, p-toluenesulfonic, and cyclohexanesulfamic acids. Typical salts are the chloride, sulfate, bisulfate, mesylate, besylate, esylate, phosphate, oxalate, maleate, succinate, citrate, malonate, and/or fumarate salts. Also included within the scope of this invention are the salts of the compound of this invention with one or more amino acids, typically naturally-occurring amino acids such as one of the amino acids found in proteins. The acidic counterion desirably is physiologically innocuous and non-toxic or otherwise pharmaceutically acceptable, unless the salt is being used as an intermediate in preparation of the compounds whereupon toxicity is not relevant. Ordinarily, compound (1) will be administered as the free base, but suitable salts include mesylate (methanesulfonic acid) and HCl.

The compound of this invention includes the solvates formed with the compound of this invention or their salts, such as for example hydrates, alcoholates and the like.

The pharmaceutical compound of this invention optionally is formulated with conventional pharmaceutical carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (2005) and include ascorbic acid and other antioxidants, chelating agents such as EDTA, carbohydrates such as dextrin, hydroxyalkylcellulose, hydroxyalkylmethylcellulose and/or organic acids such as oleic acid or stearic acid.

The term "pharmaceutically acceptable carrier" as used herein means any material or substance formulated with the active ingredient in order to facilitate its preparation and/or its application or dissemination to the site to be treated. Suitable pharmaceutical carriers for use in the compositions of this invention are well known to those skilled in the art. They include additives such as wetting agents, dispersing agents, adhesives, emulsifying agents, solvents, glidants, coatings, antibacterial and antifungal agents (for example phenol, sorbic acid, chlorobutanol), and isotonic agents (such as sugars or sodium chloride), provided that the same are consistent with pharmaceutical practice, i.e. they are not toxic to mammals.

The pharmaceutical compositions of the present invention are prepared in any known manner, for instance by homogeneously mixing, coating and/or grinding the active ingredients in a one-step or multi-step procedure, with the selected carrier material and, where appropriate, other additives such as surface-active agents. Compositions containing the compound of this invention formulated into microspheres (usually having a diameter of about 1 to 10 gm) are useful as controlled or sustained release formulations.

In one optional formulation, compound (1) is comminuted to a finely divided form, typically to an average particle size at any point within the range of about 1-20 microns. The product of example 1 is rods or needles and exhibits a range of crystal length, typically about 25-40 microns. These optionally are micronized in a Jet mill-00 at about 60-80 psi to obtain particles of about 3-4 microns and having surface area of about 7-8 square meters/g. However, the starting crystal sizes will vary from lot to lot and the degree of micronization is a matter of choice. Accordingly, micronized crystalline compound (1) is simply defined as crystal or amorphous compound (1) that has been subject to a micronization process such as the exemplary one described here. Neither the size nor surface area of the resulting particles is critical. The micronized compound (1) is suspended in aqueous solution, optionally aided by a suspending agent, emulsifiers and/or surfactant as further described below.

Typically, the pharmaceutical formulation is a solubilized form of compound (1) where crystalline compound (1) is dissolved in an appropriate solvent or solubilizing agent, or combinations thereof. Crystalline compound (1) is solubilized in a pharmaceutically acceptable excipient for administration therapeutically or prophylactically.

Suitable solutions of compound (1) for pharmaceutical preparations include water together with various organic acids (typically C4-C24) usually fatty acids like capric, oleic, lauric, capric, palmitic and/or myristic acid. The fatty acids are optionally saturated or unsaturated, or mixtures thereof. In addition, polyethylene glycols (PEGs) and/or short, medium, or long chain mono, di, or triglycerides are employed supplementary to, or in place of, the organic acids. Pegylated short, medium or long chain fatty acids optionally also are used in the same fashion.

The most common organic acids are the carboxylic acids whose acidity is associated with the carboxyl group —COOH. Sulfonic acids, containing the group $OSO_3H$, are relatively stronger acids for use herein. In general, the acid desirably contains a lipophilic domain. Mono- or di-carboxylic acids are suitable.

Suitable surface-active agents optionally are used with any of the formulations of this invention (any one or more of the following agents, typically any one of them). Such agents also are known as emulgents or emulsifiers, and are useful in the pharmaceutical compositions of the present invention. They are non-ionic, cationic and/or anionic materials having suitable emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures. Aqueous emulsions with such agents are within the scope of this invention.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8-C22 alkyl radical (e.g. cetyl, lauryl, palmityl, myristyl and oleyl) and, as further substituents, unsubstituted or halogenated lower alkyl, benzyl and/or hydroxy-lower alkyl radicals.

A more detailed description of surface-active agents suitable for this purpose is found in "McCutcheon's Detergents and Emulsifiers Annual" (MC Publishing Crop., Ridgewood, N.J., 1981), "Tensid-Taschenbucw", 2nd ed. (Hanser Verlag, Vienna, 1981) and "Encyclopedia of Surfactants," (Chemical Publishing Co., New York, 1981).

The compound of this invention is administered by any route appropriate to the condition to be treated, such as oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient, but is generally oral.

Formulations of the compound of this invention for oral administration usually are presented as discrete units such as capsules, cachets or tablets each containing a predetermined amount of the active ingredient; as a powder or granular form; as a solution or suspension in an aqueous liquid or a non-aqueous liquid; or as an oil-in-water liquid emulsion or a water-in-oil liquid emulsion. The compound of this invention optionally is presented as a bolus, electuary or paste.

A tablet is made by compression or molding, optionally with one or more accessory ingredients. Compressed tablets are prepared by compressing in a suitable machine the compound of the invention in a free-flowing form such as a powder or granules, optionally mixed with a binder, lubricant, inert diluent, preservative, surface active and/or dispersing agent. Molded tablets typically are made by molding in a suitable machine a mixture of the powdered compound moistened with an inert liquid diluent. The tablets may optionally be coated or scored and may be formulated so as to provide slow or controlled release of the active ingredient therein.

The formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the compound is employed with a paraffinic or a water-miscible ointment base. Alternatively, the compound is formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention is constituted from known ingredients in a known manner. While this phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by aerosol or powder inhalers, of which numerous examples are available. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations are presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compound of this invention optionally is formulated into controlled release compositions in which the release of the compound is controlled and regulated to allow less frequency dosing or to improve the pharmacokinetic or toxicity profile of the invention compound. Controlled release compositions are prepared in accord with known methods, many of which involve formulating the active compound with one or more polymer carriers such a polyester, polyamino acid, polyvinyl pyrrolidone, ethylene-vinyl acetate copolymer, methylcellulose, carboxymethylcellulose and/or protamine sulfate. The rate of drug release and duration of action optionally is controlled by incorporating the active ingredient into particles, e.g. microcapsules, of a polymeric substance such as hydrogels, polylactic acid, hydroxymethylcellulose, polymethyl methacrylate and the other above-described polymers. Also suitable are colloid drug delivery systems such as liposomes, microspheres, microemulsions, nanoparticles, nanocapsules and so on. Depending on the route of administration, the pharmaceutical composition, e.g., tablets, may require protective coatings.

The invention will be more fully appreciated by reference to the following examples, which are to be considered merely illustrative and not limiting the scope of the invention.

Composition percentages are by weight unless otherwise apparent from the context.

EXAMPLE 1

Synthesis of Crystalline 5-((6-(2,4-Bis(trifluoromethyl)phenyl]pyridazin-3-yl)methyl)-2-(2-fluorophenyl)-5H-imidazo[4,5-c]pyridine Scheme 1

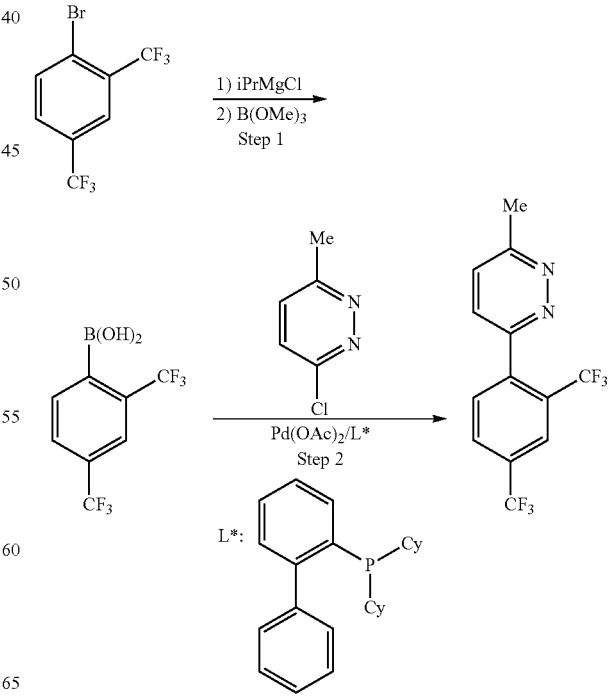

-continued

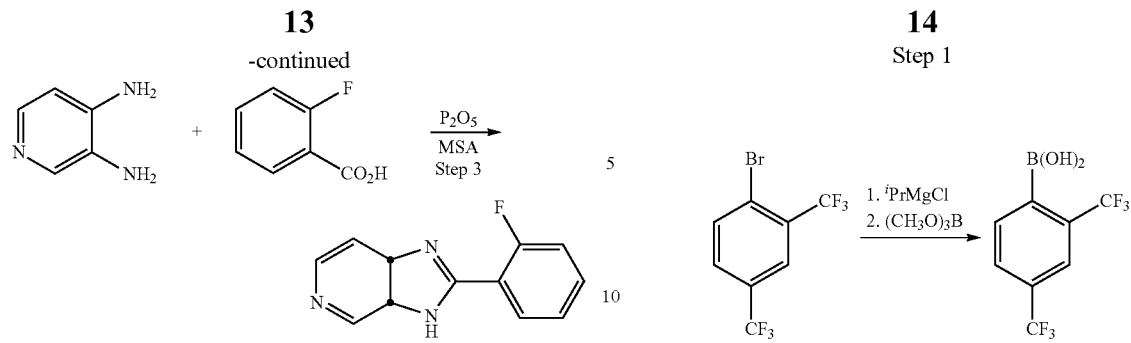

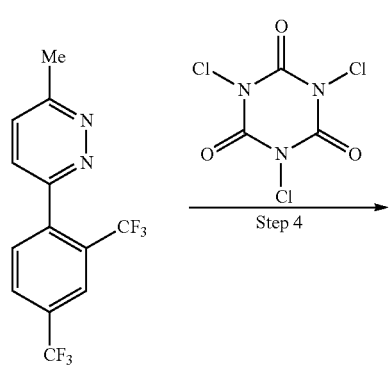

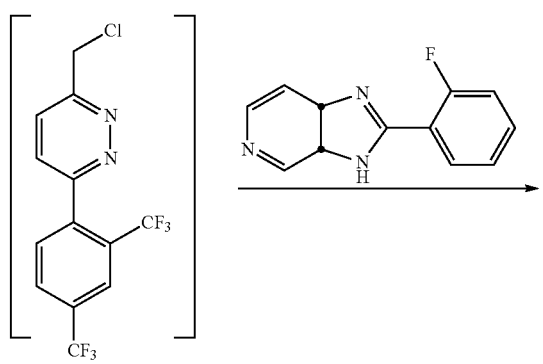

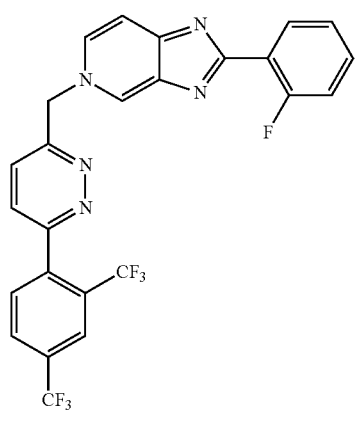

Step 1

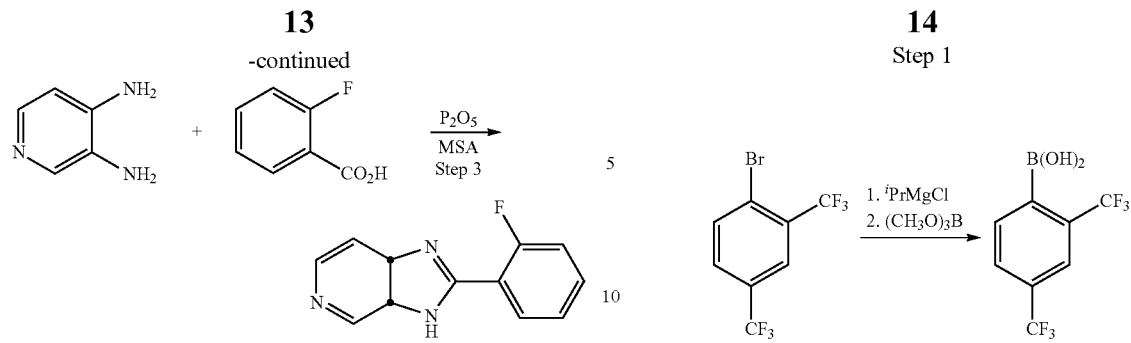

To a reactor, containing 2,4-bis(trifluoromethyl)bromobenzene (1.00 eq) and tetrahydrofuran (THF), was charged Isopropyl magnesium chloride ($^i$PrMgCl) (2 M in THF, 1.14 eq) while maintaining the content at −10° C. The mixture was agitated at −10° C. until the reaction was completed by HPLC analysis. The resultant mixture was transferred to the second reactor, containing trimethyl borate (2.26 eq) and THF held at a temperature of −10° C. The reaction was then monitored by HPLC until 1,3-bis(trifluoromethyl)benzene was not more than 2%. Aq. HCl (aqueous hydrochloric acid), prepared from water and concentrated 37% hydrochloric acid (HCl) were then added to quench the reaction while maintaining the content at not more than 25° C. After agitating the content for 1-2 h and settling for ca. 30 minutes, the layers were separated. The organic layer was washed with brine solution mixed with water and then concentrated under vacuum. Heptane was charged and the content was further concentrated under vacuum. The operations were repeated one more time. Heptane was then charged and the resultant slurry is cooled to 3° C., and agitated at the temperature for 4-6 h.

The product was filtered, washed with heptane twice and dried under vacuum at a maximum of 40° C.

| Material | M.W. | v/w Ratio | w/w Ratio | Mole Ratio |
|---|---|---|---|---|
| 2,4-Bis(trifluoromethyl)-bromobenzene | 293.00 | — | 1.00 | 1.00 |
| Heptanes | 100.21 | 13.20 | 9.00 | — |
| Hydrochloric acid, concentrated (37%) | 36.50 | 0.42 | 0.50 | — |
| Isopropyl magnesium chloride (2M in Tetrahydrofuran) | 102.85 | 1.95 | 1.90 | 1.14 |
| Sodium Chloride (NaCl) | 58.11 | — | 0.60 | — |
| Tetrahydrofuran (THF) | 72.11 | 4.50 | 4.00 | — |
| Trimethyl borate | 103.91 | 0.86 | 0.80 | 2.26 |
| Water | 18.02 | 8.90 | 8.90 | — |

Step 2

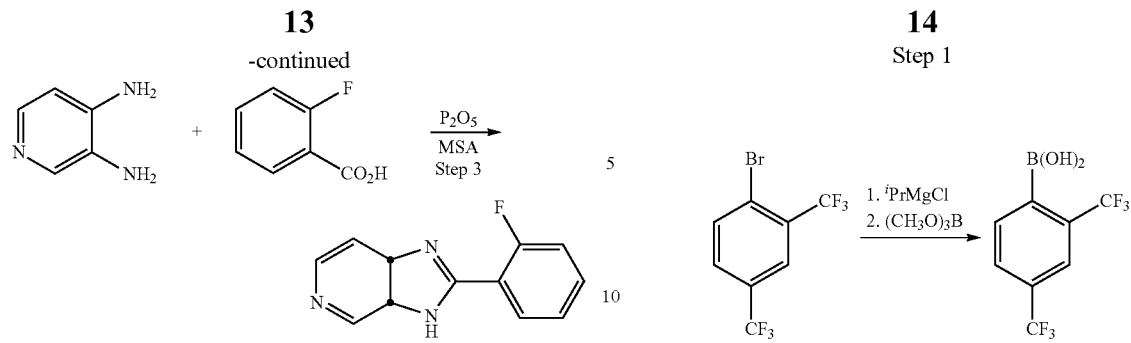

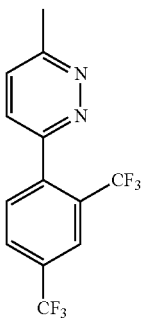

Compound 2a

3-Chloro-6-methylpyridazine (1.00 eq), 2-(dicyclohexylphosphino)biphenyl (0.05 eq), 2,4-bis(trifluoromethyl)phenylboronic acid (1.85 eq), 1,2-dimethoxyethane and aqueous potassium carbonate solution were all charged into a reactor. After degassing three times with nitrogen, palladium acetate (0.025 eq) was charged and the content is heated and agitated under reflux until the reaction was deemed complete.

The reaction mixture was cooled to 22° C. Heptane was charged, followed by addition of Celite. After agitating for ca. 30 minutes at 22° C., the mixture was filtered into the first reactor, rinsing forward with a mixture of 1,2-dimethoxyethane and Heptanes. The layers of the filtrate are separated.

To the organic layer was charged borane trimethylamine complex (0.03 eq), water, and acetic acid. The resultant mixture with a pH at maximum 4 was agitated for 1-2 h at 22° C. and then refluxed at ca. 80° C. for 2-3 h. After cooling back to 22° C., the mixture was adjusted to pH 10-11 with addition of 5% aq. sodium hydroxide while maintaining the content at 22° C. and then agitated for 1-2 h. The mixture was filtered and the layers were separated. The aq. layer was disposed of and the organic layer was filtered through ZetaCarbon cartridges into the in-process cleaned first reactor, rinsing forward with 1,2-dimethoxyethane through the carbon cartridges.

The filtrate was concentrated under vacuum with a maximum jacket setting of 60° C. Heptane was charged and the contents were further concentrated under vacuum with a maximum jacket setting of 60° C. Additional Heptane was charged to the concentrate and the 1,2-dimethoxyethane (DME) content (maximum 0.5%) of the mixture was checked by NMR. After adjusting to 85° C. and agitating for ca. 1 h, the mixture was polish filtered hot through a filter into the second reactor.

The filtrate in the second reactor was adjusted to reflux and then agitated for 1 h. With ramp cooling and moderate agitation, the mixture is cooled from reflux to 0 to 6° C. over a period of minimum 4 h and then agitated at 0 to 6° C. for 1 h.

The product was filtered, washed with ambient temperature Heptanes and dried under vacuum at a maximum of 40° C. until loss on drying is maximum 1%.

| Materials | M.W. | w/w Ratio | Mole Ratio | v/v Ratio |
|---|---|---|---|---|
| 2,4-Bis(trifluoromethyl)phenyl-boronic acid | 257.92 | 4.00 | 1.85 | — |
| Borane trimethylamine complex | 72.92 | 0.018 | 0.03 | — |
| 3-Chloro-6-methylpyridazine | 128.56 | 1.00 | 1.00 | — |
| Diatomaceous earth (celite) | N/A | 0.30 | — | — |
| Di(cyclohexyl)phosphinobiphenyl | 350.49 | 0.14 | 0.05 | — |
| 1,2-Dimethoxyethane | 90.12 | 12.00 | — | 13.80 |
| Drinking water | 18.02 | 3.75 | — | 3.75 |
| Glacial acetic acid | 60.05 | 0.05 | 0.10 | — |
| Heptanes | 100.21 | 20.40 | — | 29.80 |
| Palladium (II) acetate | 224.49 | 0.044 | 0.025 | — |
| Potassium carbonate, | 138.21 | 2.15 | 2.00 | — |
| Sodium hydroxide, 5% solution | 40.00 | — | — | — |

Step 3

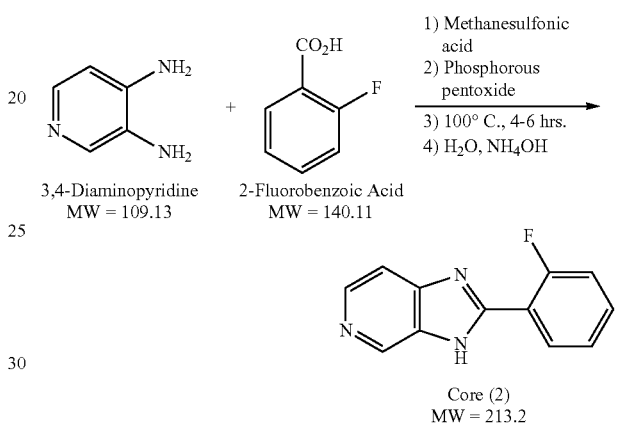

To a reactor was charged methanesulfonic acid, followed by phosphorus pentoxide (1.00 eq) in portions while maintaining the content at 23° C. 3,4-Diaminopyridine (1.00 eq) was charged in portions while maintaining the content at 20 to a maximum of 50° C. 2-Fluorobenzoic acid (1.09 eq) was then charged. The mixture was heated to 100° C. and the reaction was monitored by HPLC until completion.

The content was adjusted to 10° C. and water was charged while maintaining the content at a maximum of 25° C. After agitating the mixture at this temperature for 1 h, it was filtered into a second reactor.

To the filtrate in the second reactor was charged 27% ammonium hydroxide until the pH was in between 6.0-6.5. The content temperature was kept at a maximum of 30° C. The resultant thin slurry was agitated at 22° C. for a minimum of 1 h and 27% ammonium hydroxide was further charged, until the pH was between 8.0-9.3. The slurry was further agitated at 22° C. for a minimum of 2 h.

The product was filtered, washed with water twice, and dried at a maximum of 60° C. under vacuum, until the water content is not more than 1%. If necessary, the product is milled to remove large lumps.

| Materials | M.W. | w/w Ratio | Mole Ratio | v/v Ratio |
|---|---|---|---|---|
| Ammonium hydroxide, 27% | 35.05 | — | — | — |
| 3,4-Diaminopyridine | 109.13 | 1.00 | 1.00 | — |
| Drinking water | 18.02 | 24.00 | — | 24.00 |
| 2-Fluorobenzoic acid | 140.11 | 1.40 | 1.09 | — |
| Methanesulfonic acid | 96.10 | 7.00 | — | 4.70 |
| Phosphorous pentoxide | 141.94 | 1.30 | 1.00 | — |

Step 4

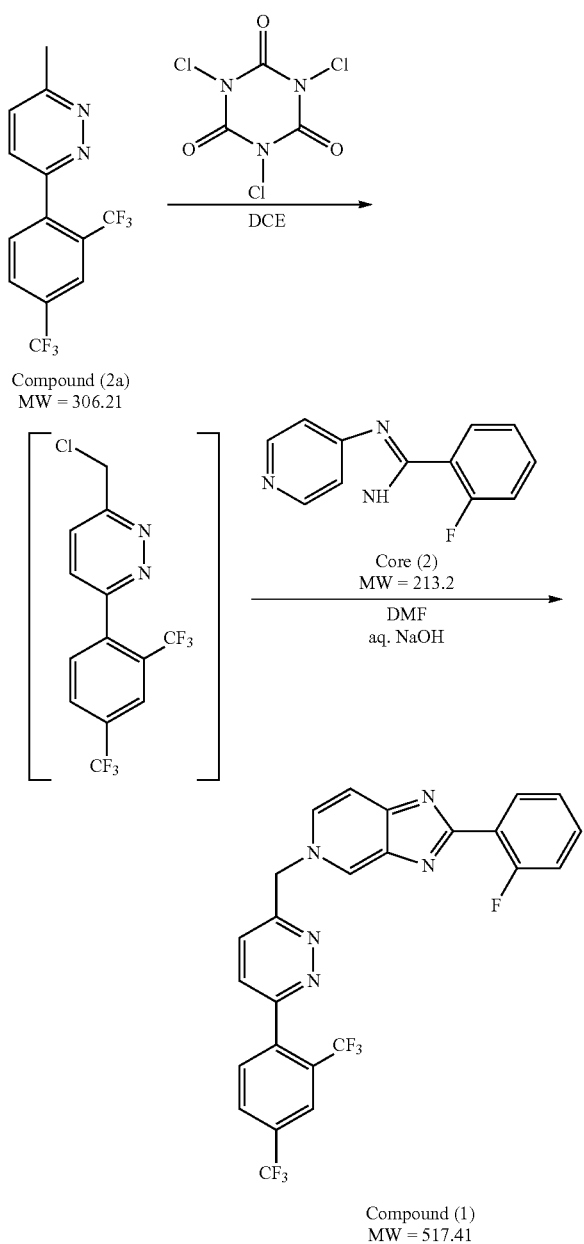

To a reactor is charged compound 2a (1.24 eq), methylene chloride and trichloroisocyanuric acid (0.491 eq). The mixture was adjusted to reflux and agitated under reflux until the reaction is complete.

The reaction mixture was cooled to 22° C. and celite was charged. After agitating for minimum of 30 minutes, the mixture was filtered into and rinsed forward with methylene chloride 3 times into the second reactor. The filter cake was disposed of. To the filtrate in the second reactor was charged 3% aq. sodium hydroxide whilst maintaining the contents at 22° C. The mixture was agitated for 1-2 h and the layers were separated. The bottom organic layer was transferred to the in-process cleaned first reactor and concentrated under vacuum with a maximum jacket temperature of 45° C. Methylene chloride was charged and the mixture was polish filtered to the in-process cleaned second reactor.

The filtrate was concentrated under vacuum with a maximum jacket temperature of 45° C. Dimethylformamide (DMF) was charged and the contents are further concentrated. The mixture was adjusted to 22° C. and DMF was charged, followed by compound core 2 (1.00 eq) and 10% aq. sodium hydroxide while maintaining the content at 22° C. The resultant mixture was agitated at 22° C. until the reaction was monitored by HPLC analysis. Over the reaction period, the pH of the content was monitored and 10% aq. sodium hydroxide was added as required to maintain the pH at 11-12 by pH meter. After the reaction, 10% aq. sodium hydroxide was charged while maintaining the contents at 22° C. The mixture was diluted with DMF and agitated for 2 h. The mixture was filtered over a minimum of 1 h into the first in-process cleaned first reactor, containing water, whilst maintaining the contents at 16° C. and then rinsing forward with DMF. The resultant slurry was agitated for 1-3 h at 22° C.

The crude product was filtered and washed with water and then methyl tertiary butyl ether (MTBE). The wet crude product was discharged from the filter and transferred into the first reactor; and ethyl acetate (EtOAc) was charged. The mixture was heated to reflux and agitated at reflux temperature until all the solids are dissolved. The water level must be less than 6.0%. With ramp cooling, the content was adjusted to 22° C. over a minimum of 4 h.

The crystallized product was filtered and washed with EtOAc and then charged back to the first reactor. Ethyl acetate (EtOAc) was added. The mixture was heated to reflux and agitated at the temperature until all the solids are dissolved. The water level must be not less than 1.0%. The mixture was filtered, hot, through a polishing filter into the second reactor (EtOAC preconditioned), rinsed forward with EtOAc.

The product was concentrated under atmospheric pressure. After adjusting to 65° C. and charging in EtOAc, the pot was adjusted to reflux and agitated at reflux for ca. 30 minutes. Water content was checked and if the water level was more than 0.2%, the same cycle was repeated.

Once the water level was at maximum 0.2%, the content was adjusted to reflux and then agitated under reflux for 1-3 h. With ramp cooling, the content was adjusted to 22° C. over minimum 4 h and then agitated at the temperature for minimum of 8 h.

The product was filtered, washed with EtOAc and dried under vacuum at maximum of 60° C. The product was then milled.

| Materials | M.W. | w/w Ratio | Mole Ratio | v/v Ratio |
|---|---|---|---|---|
| 3-(2,4-Bis(trifluoromethyl)-phenyl)-6-methylpyridazine, | 306.21 | 1.00 | 1.00 | — |
| t-Butyl methyl ether | 88.15 | — | — | — |
| Diatomaceous Earth (Celite) | | — | — | — |
| N,N-Dimethylformamide | 73.10 | 6.90 | — | 7.30 |
| Drinking water | 18.02 | 27.72 | — | 27.72 |
| Ethyl acetate | 88.11 | 33.90 | — | 37.70 |
| 2-(2-Fluorophenyl)-imidazo-[4,5-c]pyridine, GS-9133 | 213.21 | 0.560 | 0.78 | — |
| Methylene chloride | 84.93 | 16.50 | — | 12.50 |
| Sodium hydroxide | 40.00 | 0.276 | — | — |
| Trichloroisocyanuric acid | 232.41 | 0.315 | 0.415 | — |

Nuclear Magnetic Resonance ($^1$H-, $^{13}$C-, and $^{19}$F-NMR) Spectra

Nuclear magnetic resonance (NMR) spectra of compound (1) is consistent with the proposed structure. The $^{13}$C, $^{19}$F, and $^1$H-NMR spectra of compound (1) in DMSO-$d_6$ were measured using a Varian UnityInova-400 FT-NMR spectrometer. Spectra are shown in the table below. The NMR chemical shift assignments were established using 2D correlation experiments (COSY, HSQC, HMBC and HSQCTOCSY).

$^1$H- and $^{13}$C-NMR chemical shift assignments for Compound (1) reference standard

| Atom | δC/ppm (DMSO-$d_6$) | δF/ppm (DMSO-$d_6$) | δH/ppm (DMSO-$d_6$) |
|---|---|---|---|
| 1A | 140.16 | | |
| 2A | 128.32 (q$^a$, J$_{CF}$ = 32 Hz) | | |
| 3A | 123.61, m | | 8.24 (m, 1 H) |
| 4A | 130.27 (q, J$_{CF}$ = 34 Hz) | | |
| 5A | 129.54 (q, J$_{CF}$ = 3 Hz) | | 8.22 (m, 1 H) |
| 6A | 133.36 | | 7.88 (m, 1 H) |
| 7A | 123.20 (q, J$_{CF}$ = 273 Hz) | −56.4$^b$ | |
| 8A | 123.02 (q, J$_{CF}$ = 275 Hz) | −62.0$^b$ | |
| 1 | 158.76 | | |
| 2B | 128.16 | | 8.01 (d, 1 H, J = 8.4 Hz) |
| 3B | 126.20 | | 7.95 (d, 1 H, J = 8.8 Hz) |
| 4B | 157.70 | | |
| 5B | 60.49 | | 6.17 (s, 2 H) |
| 2C | 131.86 | | 8.31 (m, 1 H) |
| 3C | 112.63 | | 7.86 (m, 1 H) |
| 4C | 155.44 | | |
| 6C | 168.11 (d, J$_{CF}$ = 6 Hz) | | |
| 8C | 145.08 | | |
| 9C | 133.06 | | 9.25 (s, 1 H) |
| 1D | 123.11 (d, J$_{CF}$ = 10 Hz) | | |
| 2D | 160.46 (d, J$_{CF}$ = 254 Hz) | −111.7 | |
| 3D | 116.59 (d, J$_{CF}$ = 22 Hz) | | 7.29 (m, 1 H) |
| 4D | 130.84 (d, J$_{CF}$ = 8 Hz) | | 7.46 (m, 1 H) |
| 5D | 124.13 (d, J$_{CF}$ = 4 Hz) | | 7.31 (m, 1 H) |
| 6D | 131.72 (d, J$_{CF}$ = 2 Hz) | | 8.35 (m, 1 H) |

$^a$multiplicity, s: singlet, d: doublet, q: quartet, m: multiplet
$^b$interchangeable signals Differential Scanning Calorimetry Compound (1) samples (amorphous) designated "Research lot 6" were made according to the method published as Example 1a in WO 08/005519, which is hereby incorporated by reference in its entirety. The remaining samples were crystalline compound (1). The samples were subjected to measurement using a Differential Scanning calorimetry (DSC) apparatus (DSC2010, manufactured by TA Instruments Corporation), under nitrogen atmosphere, sample weight 5±1 mg, temperature rise rate: either 1° C. per min, 5° C. per min or 10° C. per min, open aluminum pan, and indium standard as a reference. The enthalpy, extrapolated onset temperature and apex temperature at an endothermic peak on the obtained DSC curve were determined.

Figure 4:
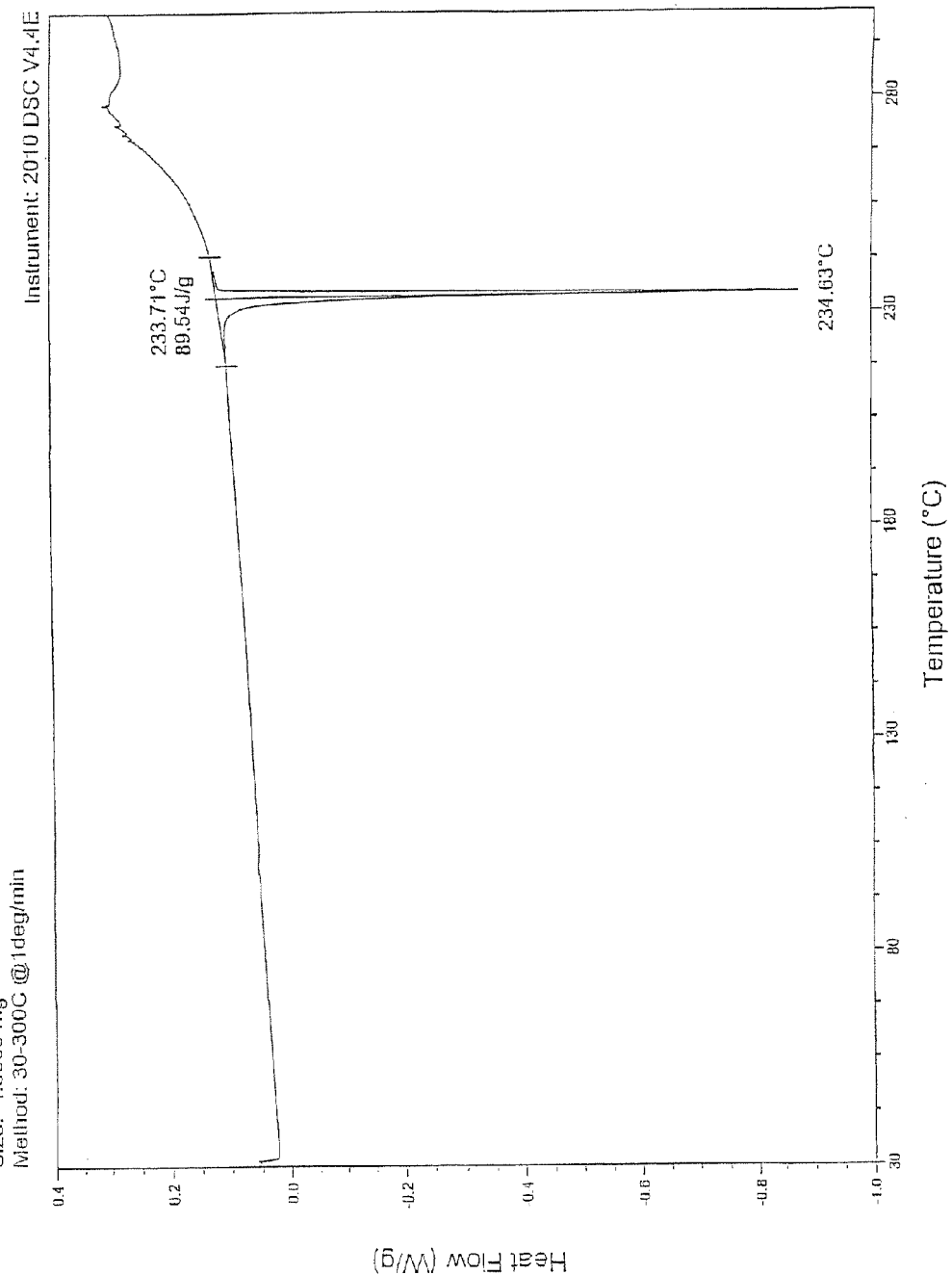
FIG. 4 illustrates a DSC thermogram obtained for crystalline compound (1) reference standard, 1° C./min scan, obtained by the method of Example 1 below.
Figure 5:
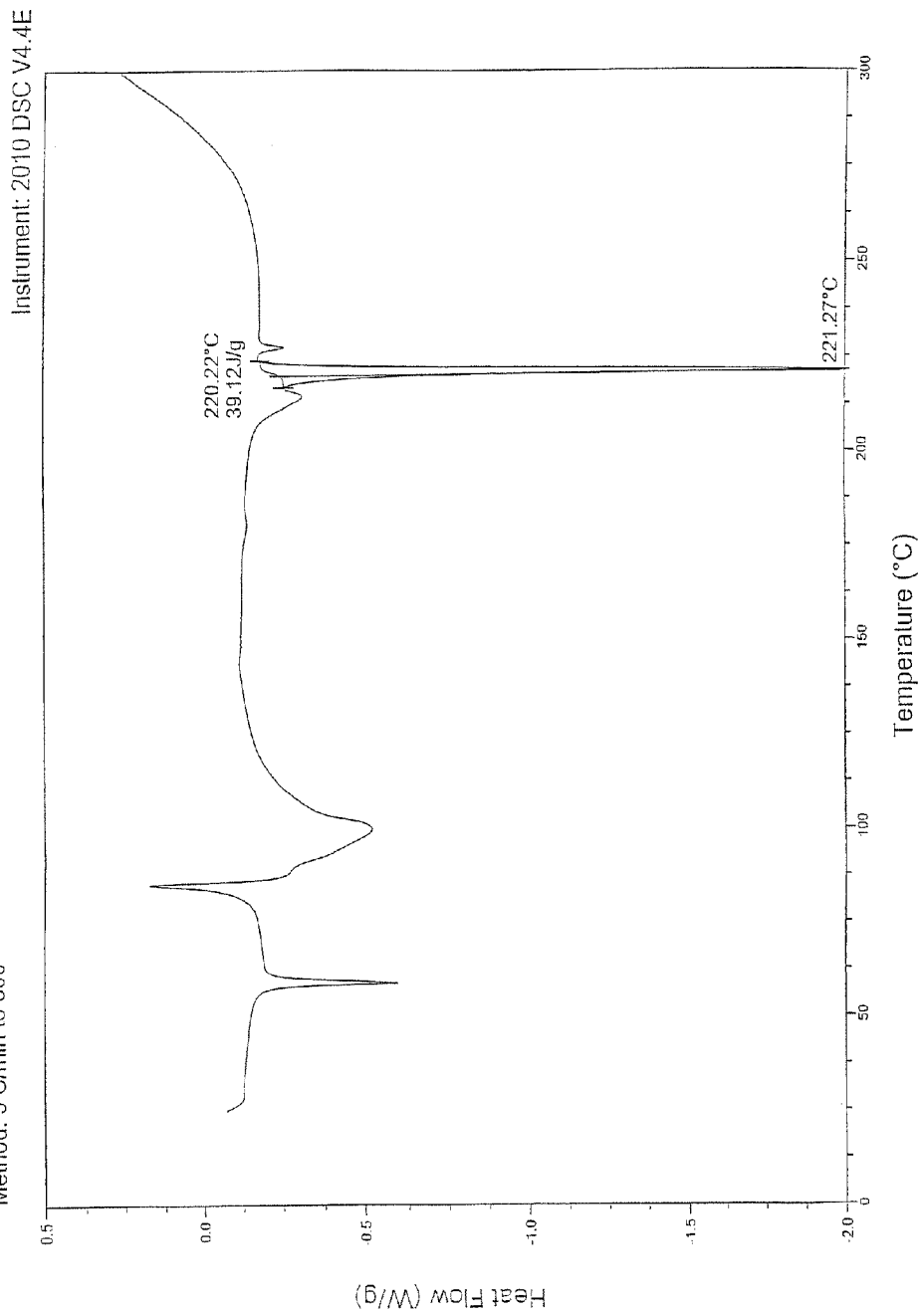
FIG. 5 shows a DSC thermogram obtained for the amorphous form of compound (1) Research Lot 6, 5° C./min scan, obtained by the method of Example 1a in WO 08/005519.

The DSC results for Research lot 6 and representative crystalline free base compound (1) batches are summarized in Table 1 and FIGS. 4 and 5, respectively. When the crystal form of compound (1) was subjected to DSC scan at 1° C./min, the enthalpy of the endothermic peak is about 80 J/g, and the extrapolated onset temperature is 233.2° C.±2.0° C. The apex of the endothermic peak is 233.9° C.±3.0° C.

TABLE 1

Example DSC values obtained for Compound (1) batches

| | 10° C./min scan | | 1° C./min scan | | |
|---|---|---|---|---|---|
| | peak onset | main peak | peak onset | main peak | Enthalpy (J/g) |
| 9190 Ref Std | 235.8 | 237.2 | 233.7 | 234.6 | 89.5 |
| 9190-A-1 | n/a | n/a | 234.8 | 234.0 | — |
| 9190-B-1 Crop 1 | 235.2 | 237.4 | 231.6 | 232.2 | 78.5 |
| 9190-B-1 Crop 2 | 236.1 | 238.5 | 234.3 | 235.6 | 80.9 |
| **Research Lot 6 | 220.2 | 221.3 | pending | pending | 39.1 |

Note:
All ° C. exceept for enthalpy
**5° C./min scan reported for Lot 6

X-Ray Powder Diffractometry—Study 1

Samples made by example 1a of WO 05/063744 and by the method of this invention were analyzed in the as received condition, only mixing with a spatula prior to analysis. A sample was fixed to an aluminum cell, and the measurement was performed using an X-ray powder diffractometer (XRD-6000, Shimadzu Lab X, manufactured by Shimadzu Corporation, X-ray source: Cu—Kα1 ray, tube voltage: 35 kV, tube electric current: 40 mA, scan speed: 2° per min, continuous scan mode, sampling pitch: 0.02°, scan range: 4-35°, β axis rotation: 60 rpm).

Non-micronized, ascicular compound (1) crystals obtained by the method of this invention have an X-ray powder diffraction pattern having characteristic diffraction peaks at diffraction angles 2θ (°) of 13.46, 15.59, 16.90, 17.48, 23.05 and 30.15 as measured by X-ray powder diffractometer (FIG. 1). Note that the non-micronized "high melt" 235° C. melt ascicular crystal form of compound (1) tested in this example shows some effects due to preferred orientation and particle size. As a result, FIG. 1 should be considered merely exemplary because varying the crystal size and orientation will change the magnitude of the peaks in the plot. Additionally, the diffraction peak value at the above mentioned diffraction angle 2θ (°) may show slight measurement error due to the measurement instrument or measurement conditions and the like. Typically, the measurement error generally is within the range of about ±0.3. The specification for the Shimadzu XRD-6000 is ±0.04. Further, some variation in peak positions can be expected due to product and experimental variation, so they must be considered approximate.

The 220° C. "low melt" solid state form of compound (1) comprised by product made according to the example 1a method (or in the method herein prior to the reslurry step) gives an X-ray powder diffraction pattern consistent with amorphous material (FIG. 3).

Compound (1) by the method of this invention typically exhibits intrinsic solubility of 0.7 micrograms/ml, a pKa of 5.8, log P of 2.8; and geometric mean (3 lots) pH solubility profile at pH 2 of 458 micrograms/ml and at pH 7.3, 0.7 micrograms/ml. Geometric mean solubility (3 lots) in simulated intestinal fluids (fasted: pH 6.4, 0.75 mM lecithin, 3 mM sodium taurocholate, 270 mOsmol; fed: pH 5.0, 3.75 mM lecithin, 15 mM sodium taurocholate, 635 mOsmol) were 19.1 micrograms/ml (fasted) and 122 micrograms/ml (fed).

Measured parameters vary from lot to lot, so all of the foregoing parameters except molecular weight should be considered to be approximate.

Titration with acids revealed higher solubility with mesylate (>20 mg/ml) compared to the chloride (about 0.6 mg/mL) or sulfate (about 0.5 mg/mL) counterions.

X-Ray Powder Diffractometry—Study 2

Another sample of crystalline compound (1) prepared by the method of this invention was analyzed in the same fashion as Study 1 except that the X-ray powder diffractometer was a PANalytical X'Pert Pro MPD PW3040 Pro, manufactured by PANalytical Inc., using X-ray source: Cu—Kα ray (1.54059 Å), tube voltage: 45 kV, amperage: 40 mA, scan range: 1-55° 2θ, step size: 0.008° 2θ, collection time: 3373 s, scan speed: 0.9° per min, slit: DS: ½°, SS: ¼°, revolution time: 0.5 s, mode: transmission. The results are depicted in FIG. 2.

EXAMPLE 2

Formulation of Compositions Using Compound (1)

Crystalline compound (1) is used as an intermediate to produce pharmaceutically acceptable solutions. The following examples are made on a weight by weight basis to achieve 10% w/w active. To make 12 kg solution, exemplary quantitative compositions of compound (1) capsules, 20 mg and 40 mg are listed below.

Quantitative composition of Compound (1) capsules, 20 mg and 40 mg

| Components | % w/w | Capsule Unit Formula (mg/unit) 20 mg | Capsule Unit Formula (mg/unit) 40 mg | Compendial Reference | Function |
|---|---|---|---|---|---|
| Compound 1 | 10.00 | 20.0 | 40.0 | None | Active ingredient |
| Oleic Acid | 84.55 | 169.1 | 338.2 | NF | Solvent |
| Polysorbate 80 | 5.00 | 10.0 | 20.0 | NF | Surfactant |
| Butylated Hydroxytoluene (BHT) | 0.10 | 0.2 | 0.4 | NF | Antioxidant |
| Butylated Hydroxyanisole (BHA) | 0.35 | 0.7 | 1.4 | NF | Antioxidant |
| Capsule Sealing Solution[a] | | | | | Capsule sealant |
| Ethanol | —[b] | —[b] | —[b] | USP | — |
| Purified water | —[b] | —[b] | —[b] | USP | — |
| Capsule Shell, Size 0 Licaps™ White Opaque | N/A | 1 each | 1 each | None | Capsule shell |
| Total | 100.00 | 200.0 | 400.0 | | |

[a]Composition is 1:1 w/w ethanol:water solution.
[b]Removed during the capsule sealing process.

Container/vessel: 12 kg stainless steel
Weigh the following in order:
0.012 kg butylated hydroxytoluene (0.10%)
0.035 kg butylated hydroxyanisole (0.35%)
1.2 kg Compound (1) free base (10%).
0.6 kg Polysorbate 80 (5%) weighed
10.153 kg oleic Acid (equivalent to 84.55 g (84.55%))

Solubilized crystalline compound (1) capsules, 20 mg or 40 mg, are manufactured through a series of unit process steps. Compound (1) drug substance, oleic acid, polysorbate 80, butylated hydroxytoluene (BHT), and butylated hydroxyanisole (BHA) are mixed until a solution is achieved. The solution is filled into 2-piece hard gelatin capsules. Closed capsules are subsequently sealed with a hydroalcoholic solution, which is evaporated during the sealing process. A vacuum leak test is performed on sealed capsules prior to packaging.

Alternative Formulations

The crystalline compound of formula (1) optionally is used as an intermediate to be formulated into a solubilized form with the following agents:
  Fatty acids (short, medium, and long chained as well as saturated and unsaturated), typically C4 to C22. Typical fatty acids are linoleic acid, lauric acid, capric acid or oleic acid.
  Alcohols such as ethanol, benzyl alcohol, glycerol, polyethylene glycol 200, polyethylene glycol 300, polyethylene glycol 400.
  Surfactants, including both ionic and non-ionic surfactants. Examples of non-ionic surfactants are fatty acid esters of polyoxyethylene sorbitan, sorbitan fatty acid ester, polyoxyethylene castor oil derivatives, polyoxyethleneglycerol oxystearate, polyethyleneglycol 60, hydrogenated castor oil, and/or block copolymers of ethylene oxide and propylene oxide.
  Antioxidants, for example butylated hydroxyanisole (BHA), butylated hydroxytoluene (BHT), ascorbyl palmitate, vitamin E, and/or vitamin E PEG 1000 succinate for chemical stability.
  Viscosity inducer (silicon dioxide, polyethylene glycols, titanium oxide and the like).
  And mixtures of the above Encapsulation can be performed in a soft elastic gelatin or a hard gelatin or a hard hydroxypropyl methyl cellulose capsule. The liquid formulation (solution or encapsulated solution) provides improved oral bioavailability.

Capsule Filling

The composition and preparation of the soft elastic gelatin capsule is well known in the art. The composition typically comprises from 30-50% by weight gelatin, 10-40% plasticizer or a blend of plasticizers and about 25-40% by weight water. Plasticizers can be glycerin, sorbitol or sorbitol derivatives, propylene glycol and the like or a combination thereof.

Various methods can be used for manufacturing and filling the soft elastic gelatin capsules such as rotary, liner or accogel machine and the like. Hard gelatin or HPMC capsules can be purchased from Capsugel, Greenwood, S.C. and other suppliers. Capsules are filled manually or by capsule filling machine.

Formulation Preparation

In general, the compositions of this invention can be prepared in the following manner. The ingredients are mixed in an appropriate vessel size using an overhead mixer (The mixing tank may be purged with nitrogen). The pharmaceutically acceptable fatty acid and the pharmaceutically acceptable antioxidant are mixed at room temperature. (The solution may be warmed to appropriate temperature if needed, for example to about 45° C. in the case of lauric acid, in order to liquefy the fatty acid). The compound of formula (1) is added and stirred until dissolved. The pharmaceutically acceptable surfactant is added with mixing. The appropriate weight of the resulting mixture is filled into hard gelatin capsules.

Additional Formulation Compositions

| | |
|---|---|
| Formula (1) compound | 8.0 |

-continued

| | |
|---|---|
| PEG 400 | 82.8 |
| EtOH | 9.2 |
| Total | 100.0 |
| Formula (1) compound | 8.0 |
| EtOH | 11.0 |
| PG | 7.4 |
| Maisine 35-1 | 36.8 |
| Cremophor RH40 | 36.8 |
| Total | 100.0 |
| Formula (1) compound | 8.0 |
| Oleic Acid | 92.0 |
| Total | 100.0 |
| Formula (1) compound | 8.0 |
| Oleic Acid | 73.6 |
| EtOH | 9.2 |
| Tween 20 | 9.2 |
| Total | 100.0 |
| Formula (1) compound | 8.00% |
| Oleic Acid | 87.40% |
| Tween 80 | 4.60% |
| Total | 100.00% |
| FORMULA (1) COMPOUND | 20.00% |
| Oleic Acid | 80.0% |
| Total | 100.0% |
| FORMULA (1) COMPOUND | 20.00% |
| Oleic Acid | 76.00% |
| Tween 80 | 4.00% |
| Total | 100.00% |
| FORMULA (1) COMPOUND | 8.00 |
| Oleic Acid | 86.47% |
| Tween 80 | 4.60% |
| Aerosil 200 | 0.92% |
| BHT | 0.01% |
| Total | 100.0% |
| FORMULA (1) COMPOUND | 8.00 |
| Oleic Acid | 85.55% |
| Tween 80 | 4.60% |
| Aerosil 200 | 1.84% |
| BHT | 0.01% |
| Total | 100.0% |
| FORMULA (1) COMPOUND | 8.00 |
| Oleic Acid | 85.55% |
| Tween 80 | 4.60% |
| Aerosil 200 | 1.84% |
| BHT | 0.01% |
| Total | 100.0% |
| FORMULA (1) COMPOUND | 10.00 |
| Oleic Acid | 84.55% |
| Tween 80 | 5.00% |
| BHA | 0.35% |
| BHT | 0.1% |
| Total | 100.0% |

EXAMPLE 2a

Micronized Formulation of Compound (1)

Micronized drug substance (Jet mill-00 at 60-80 psi; 3-4 microns average size, about 7-8 sq. meters/g) was dry blended with lactose, microcrystalline cellulose, croscarmellose sodium, sodium lauryl sulfate, tartaric acid, and hydroxypropyl cellulose. The blend was granulated by spraying the blend solution. The granules were dried in a fluid-bed. The dried granules were sized by passing through a mill, and then blended with additional microcrystalline cellulose and croscarmellose sodium. The powder blend was lubricated by adding magnesium stearate and then compressed into tablets using a rotary tablet press. The tablets were subsequently film-coated.

The table below is a summary of various formulations tested in dogs dosed at 40 mg compound (1), corresponding to approximately 4 mg/kg. The table illustrates the superior performance of the solubilized compound (1) formulations.

| In-vivo Data Summary | | | | | | | |
|---|---|---|---|---|---|---|---|
| Dosage Form | Process | Formula | Drug Load (%) | Cmax ($\mu$M) | AUC$_{24}$ ($\mu$M hr) | F (%) | RSD (%) |
| Solid | Powder Fill[a] | PIC | 50 | 0.7 | 2.9 | 8 | 52 |
| Solubilized | Liquid Fill | Capric acid | 20 | 4.8 | 25 | 79 | 17 |
| | | Lauric acid | 20 | 2.6 | 14.3 | 44 | 29 |
| | | Oleic Acid | 8 | 3.8 | 23 | 67 | 27 |
| | | | 20 | 2.1 | 14 | 44 | 56 |
| | | | 25 | 7.9 | 42 | 125 | 24 |
| Solid | High Shear[a] | SLS only | 20 | 0.4 | 4.4 | 13 | 85 |
| | | SLS & Tartaric | 20 | 0.4 | 2.7 | 8 | 82 |
| | | SLS & Tartaric[b] | 20 | 0.9 | 6.9 | 20 | 67 |
| | Fluid bed[a] | SLS & Tartaric | 20 | 0.3 | 4.4 | 14 | 77 |

[a]Utilizes micronized API
[b]Dosed in dogs treated with pentagastrin to reduce stomach pH

EXAMPLE 3

Antiviral Activity of Compound (1)

The compound of this invention exhibits anti-HCV replicon activity (assay described in WO 05/063744) against both genotypes 1a and 1, extremely low cytotoxicity (>50,000 nM in Huh-7, HepG2 and MT4 cells), and a highly favorable selectivity index. The compound is substantially less active against genotype 2a.

Activity of Compound 1 Against HCV Genotype 1 and 1a Replicons

HCV genotype 1 (Con-1/lucneo) and 1a (H77/neo) replicon cells were incubated with serial dilutions of compound (1) 2'C-methyl adenosine (2'CMeA) or IFNα for 3 days in the absence or presence of 40 mg/mL human serum albumin (HSA). After incubation, replicon RNA levels in the treated cells were determined by either a luciferase reporter assay (1 replicon) or a quantitative real-time PCR assay (1a replicon) and the data points were used to calculate EC$_{50}$ (50% effective inhibiting concentration) values for the inhibitors. Compound (1) was shown to inhibit both genotype 1 and genotype 1a replicons with $EC_{50}$ values of 0.6 and 3.6 nM, respectively (Table A). In the presence of human serum albumin, the $EC_{50}$ value of Compound (1) was increased to 11 nM.

TABLE A

Activity of Compound (1) against HCV Genotypes 1a and 1 Replicons

| Compound | $EC_{50}$ [nM][a] | | |
|---|---|---|---|
| | HCV 1-lucneo | HCV 1-lucneo 40 mg/mL HSA | HCV-1a |
| 1 | 0.6 ± 0.28 | 11 | 3.6 ± 1.4 |
| 2'CMeA | 175 ± 70 | 250 | 170 |
| IFN-α | 2 IU/mL | n.d. | n.d. | n.d., not determined; HSA, human serum albumin
[a]Mean $EC_{50}$ value and standard error determined from at least 4 independent experiments

Activity of Compound (1) Against HCV Genotype 1a Replicon and Virus

The antiviral activity of compound (1) against HCV genotype 2a was tested in cells chronically infected with the genotype 2a virus as well as in cells replicating a subgenomic 2a replicon. Huh-7 cells containing chronically replicating HCV genotype 2a (J6/JFH-Rluc) virus or subgenomic replicons were cultured with compound (1) or 2'CMeA for 3 days in the absence of human serum albumin. After cultivation, the amount of luciferase in 2a-virus containing cells and HCV NS3 protease activity in the 2a replicon-containing cells was determined using Promega's luciferase assay and a novel time-resolved fluorescence assay, respectively.

The antiviral activity of compound (1) was significantly reduced in both the HCV-2a chronically infected cell culture model ($EC_{50}$=2.9 µM) and the 2a subgenomic replicon model ($EC_{50}$=21.9 µM) compared to Huh-7 cells replicating an HCV-1 subgenomic replicon ($EC_{50}$=0.0006 µM) (Table 2). Taken together, these results suggest that the reduction in potency for compound (1) against HCV genotype 2a may be due to the genotypic differences between genotype 1 and genotype 2 of HCV.

TABLE B

Activity of Compound (1) against HCV Genotypes 1 and 2a

| Compound | $EC_{50}$ [nM][a] | | |
|---|---|---|---|
| | HCV 1-lucneo (subgenomic replicon) | HCV 2a (subgenomic replicon) | HCV-2a (reporter virus) |
| 1 | 0.6 ± 0.28 | 21898 ± 18972 | 2900 ± 1250 |
| 2'CMeA | 175 ± 70 | 1610 ± 1099 | 194 ± 26 |
| IFN-α | 2 IU/mL | n.d. | 1.2 IU/mL | n.d., not determined; HSA, human serum albumin
[a]Mean $EC_{50}$ value and standard error determined from at least 4 independent experiments Compound (1) was evaluated for its cytotoxicity in a variety of cell types including HCV replicon-containing cell lines (Huh-7, SL3 and MH4) and non-replicon-containing cell lines (HepG2, MT4), using a CellTiter-Glo Luminescence Cell Viability assay (Promega). No toxic effects were observed in any of the cell lines at the highest concentration tested (50 µM) (Table C). These results, coupled with its potent antiviral activity ($EC_{50}$=0.62-3.6 nM) in HCV-1 and HCV-1a replicons, indicates a high selectivity index ($CC_{50}$/$EC_{50}$>13,000-80,000) for compound (1).

TABLE C

Cytotoxicity of compound (1) in HCV Replicon Containing Cell Lines

| Compound | $CC_{50}$ [µM][a] | | | | |
|---|---|---|---|---|---|
| | Huh-7 lucneo[b] | SL3[b] | MH4[b] | HepG2 | MT4 |
| 1 | >50 | >50 | >50 | >50 | >50 |
| 2'CMeA | 7.2 ± 6 | 3.9 | 16 | 24.3 ± 2.1 | 3.5 ± 1.9 | n.d., not determined; HSA, human serum albumin
[a]Mean $CC_{50}$ value and standard error determined from at least 4 independent experiments
[b]HCV replicon-containing cell lines

Anti-HCV Activity of Compound (1) in Combination with IFN In Vitro

Pegylated interteron-α (PEG-IFN-α), in combination with ribavirin, represents the current standard of care for HCV-infected patients. In vitro combination studies of compound (1) and IFN-α were performed in replicon cells. Data was analyzed using the MacSynergy template developed by Prichard and Shipman. Results from these studies suggest an additive interaction between compound (1) and IFN-α.

EXAMPLE 4

Antiviral, Pharmacokinetic and Safety Data for Compound (1) in a Phase-1, First-In-Human Trial in HCV Genotype 1-Infected Subjects A randomized, double-blind, placebo controlled trial was designed to evaluate the safety/tolerability, phamacokinetics and antiviral activity of single (in Part A) and multiple (in Part B) doses of Compound (1) (oleic acid solution, above) in subjects chronically infected with HCV genotype 1 (GT-1) without decompensated cirrhosis. Prospective subjects are 18-60 years of age, are HCV treatment naïve, and are in general good health.

In completed Part A, five successive cohorts of 6 subjects were randomized (5:1) to receive single ascending doses of Compound 1 (40, 120, 240, 240—with food, or 480 mg) or placebo. In ongoing Part B, four successive cohorts of 12 subjects are randomized (10:2) to receive multiple ascending doses of Compound 1 (40 mg BID, 120 mg BID, 240 mg QD, 240 mg BID) or placebo, over 8 days.

Thirty-one subjects enrolled in Part A were of mean age 43.6 years, predominantly male (20/31), Caucasian (25/31), and infected with either HCV Genotype-1a (24) or 1 (6). Median (range) baseline HCV viral load was 6.6 $Log^{10}$ RNA IU/mL (5.2-7.3). Single doses of compound (1) were well tolerated, with no serious or treatment-limiting adverse events (AEs) reported. The most common AE was headache. All AEs were mild in severity, with the exception of one moderate headache. There were no Grade 3 or 4 treatment emergent laboratory abnormalities.

Median compound (1) plasma half-life ranged from 10 to 15 hours across cohorts. Systemic exposure was increased approximately 2-fold when compound (1) was administered with a high fat meal. Mean compound (1) concentration 24 hours after the 240 mg fasted dose dosing was ~7-fold higher than the protein binding adjusted in vitro HCV GT-1 Replicon $EC_{50}$ value. Following single-dose exposure, maximal antiviral effect was observed at 24 hours, with median declines ranging from 0.46 to 1.49 $Log^{10}$ HCV RNA IU/mL across cohorts. Individual HCV RNA declines among all compound (1) recipients ranged from 0.19 to 2.54 $\log^{10}$ IU/mL following single-dose exposure.

This is the first clinical demonstration of antiviral activity of compound (1). Single dose exposure to compound (1) was well tolerated, demonstrated favorable PK properties and potent antiviral activity.

We claim:

1. A pharmaceutical composition comprising a compound of formula (1)

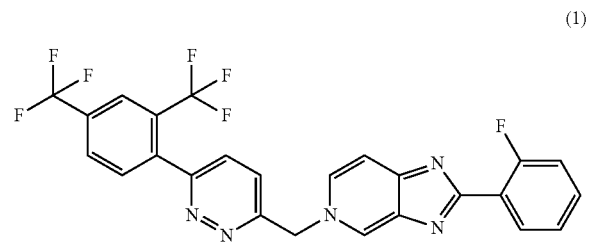 [SMILES: Fc1ccccc1-c1nc2ccn(Cc3ccc(-c4ccc(C(F)(F)F)cc4C(F)(F)F)nn3)cc-2n1]

and one or more fatty acids.

2. The pharmaceutical composition of claim 1 wherein the fatty acid is a saturated or unsaturated 4-22 carbon chain.

3. The pharmaceutical composition of claim 1 wherein the fatty acid is linoleic, oleic, lauric, palmitic or myristic acid.

4. The pharmaceutical composition of claim 1 wherein the fatty acid is oleic acid.

5. The pharmaceutical composition of claim 4 wherein compound (1) is 8% by weight and the oleic acid is 92% by weight.

6. The pharmaceutical composition of claim 1 wherein compound (1) is 20% by weight and the oleic acid is 80% by weight.

7. The pharmaceutical composition of claim 1 further comprising polyethylene glycols, or short, medium, or long chain mono, di, or triglycerides, or pegylated short, medium or long chain fatty acids.

8. The pharmaceutical composition of claim 3 further comprising one or more surfactants selected from fatty acid esters of polyoxyethylene sorbitan, sorbitan fatty acid ester, polyoxyethylene castor oil derivatives, polyoxyethleneglycerol oxystearate, polyethyleneglycol 60, hydrogenated castor oil, and block copolymers of ethylene oxide and propylene oxide.

9. The pharmaceutical composition of claim 8 wherein the fatty acid is oleic acid and the surfactant is polyoxyethylene sorbitan.

10. The pharmaceutical composition of claim 9 comprising 8% of compound (1), 87.4% of oleic acid and 4.6% of polyoxyethylene sorbitan, by weight.

11. The pharmaceutical composition of claim 9 comprising 20% of compound (1), 76% of oleic acid and 4% of polyoxyethylene sorbitan, by weight.

12. The pharmaceutical composition of claim 9 comprising 8% of compound (1), 86.47% of oleic acid, 4.6% of polyoxyethylene sorbitan, 0.92% Aerosil 200, and 0.01% BHT, by weight.

13. The pharmaceutical composition of claim 9 comprising 8% of compound (1), 85.55% of oleic acid, 4.6% of polyoxyethylene sorbitan, 1.84% Aerosil 200, and 0.01% BHT, by weight.

14. The pharmaceutical composition of claim 9 comprising 10% of compound (1), 84.55% of oleic acid, 5.00% of polyoxyethylene sorbitan, 0.35% BHA, and 0.1% BHT, by weight.

15. The pharmaceutical composition of claim 9 further comprising one or more alcohols selected from ethanol, benzyl alcohol, glycerol, polyethylene glycol 200, polyethylene glycol 300, and polyethylene glycol 400.

16. The pharmaceutical composition of claim 9 comprising 8% of compound (1), 73.6% of oleic acid, 9.2% of polyoxyethylene sorbitan, and 9.2% of ethanol, by weight.

17. A pharmaceutical dosage form comprising a compound of formula (1)

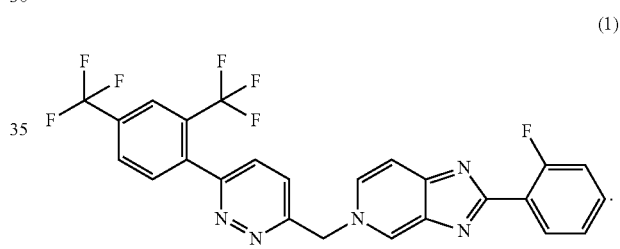

and one or more fatty acids selected from oleic, lauric, palmitic and myristic acid.

18. The pharmaceutical dosage form of claim 17 comprising oleic acid and polyoxyethylene sorbitan.

19. The pharmaceutical dosage form of claim 17 wherein the dosage form is a capsule.

* * * * *